(12) United States Patent
Friedman et al.

(10) Patent No.: US 10,045,784 B2
(45) Date of Patent: Aug. 14, 2018

(54) DEVICES AND METHODS FOR LIGATING ANATOMICAL STRUCTURES

(71) Applicant: MAYO FOUNDATION FOR MEDICAL EDUCATION AND RESEARCH, Rochester, MN (US)

(72) Inventors: Paul A. Friedman, Rochester, MN (US); Charles J. Bruce, Rochester, MN (US); Samuel J. Asirvatham, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 565 days.

(21) Appl. No.: 14/504,759

(22) Filed: Oct. 2, 2014

(65) Prior Publication Data

US 2015/0018853 A1    Jan. 15, 2015

Related U.S. Application Data

(63) Continuation of application No. 12/442,294, filed as application No. PCT/US2007/020509 on Sep. 21, 2007.

(Continued)

(51) Int. Cl.
*A61B 17/04*    (2006.01)
*A61B 17/12*    (2006.01)
(Continued)

(52) U.S. Cl.
CPC .... *A61B 17/12013* (2013.01); *A61B 18/1492* (2013.01); *A61B 2017/00243* (2013.01);
(Continued)

(58) Field of Classification Search
CPC .... A61B 17/12013; A61B 2017/00243; A61B 18/1492; A61B 2017/00867; A61B 2017/00575
See application file for complete search history.

(56) References Cited

U.S. PATENT DOCUMENTS 5,281,238 A * 1/1994 Chin ................ A61B 17/06166
606/113
5,306,234 A    4/1994 Johnson
(Continued)

FOREIGN PATENT DOCUMENTS

DE    195 34 857 C1    11/1996
FR    2 797 171 A1    2/2001

OTHER PUBLICATIONS

Bruce et al., "Device-based therapies for atrial fibrillation". *Curr. Treat. Options. Cardiovasc. Med.* 2005. 7(5):359-370.

*Primary Examiner* — Gregory Anderson
*Assistant Examiner* — Christina Lauer
(74) *Attorney, Agent, or Firm* — Mueting, Raasch & Gebhardt, P.A.

(57) ABSTRACT

Devices and methods for ligating anatomical structures are provided herein. In particular, the devices and methods provided herein can be used to ligate the left atrial appendage. The ligating devices (10, 110, 210, 310, 410) comprise a ligating element (30, 130, 230, 330, 430) and a control element (40, 140, 240, 340, 430) which controls the opening of the ligating element in a loop or lariat shape. Some embodiments comprise also a positioning element (50, 150) which help position the ligating element. In some embodiments a conduit (250) is provided for deploying the ligating element by inflating control.

20 Claims, 33 Drawing Sheets

Related U.S. Application Data

(60) Provisional application No. 60/826,413, filed on Sep. 21, 2006.

(51) Int. Cl.
*A61B 18/14* (2006.01)
*A61B 17/00* (2006.01)

(52) U.S. Cl.
CPC .............. *A61B 2017/00575* (2013.01); *A61B 2017/00867* (2013.01)

(56) References Cited

U.S. PATENT DOCUMENTS

| | | |
|---|---|---|
| 5,403,331 A | 4/1995 | Chesterfield et al. |
| 5,649,939 A | 7/1997 | Reddick |
| 5,759,189 A | 6/1998 | Ferragamo et al. |
| 5,769,863 A | 6/1998 | Garrison |
| 5,984,917 A | 11/1999 | Fleischman et al. |
| 6,132,439 A | 10/2000 | Kontos |
| 6,245,078 B1 | 6/2001 | Ouchi |
| 6,488,689 B1 | 12/2002 | Kaplan et al. |
| 6,517,550 B1 * | 2/2003 | Konya ................ A61B 17/221 606/113 |
| 6,569,082 B1 | 5/2003 | Chin |
| 6,666,861 B1 | 12/2003 | Grabek |
| 6,706,052 B1 | 3/2004 | Chin |
| 7,214,180 B2 | 5/2007 | Chin |
| 2002/0049457 A1 * | 4/2002 | Kaplan ................ A61B 17/12 606/139 |
| 2004/0030335 A1 | 2/2004 | Zenati et al. |
| 2004/0102804 A1 | 5/2004 | Chin |
| 2004/0210240 A1 | 10/2004 | Saint |
| 2005/0125006 A1 | 6/2005 | Nady |
| 2005/0154404 A1 | 7/2005 | Liddicoat et al. |
| 2005/0277959 A1 | 12/2005 | Cosgrove et al. |
| 2006/0253129 A1 | 11/2006 | Liddicoat et al. |
| 2007/0073313 A1 | 3/2007 | Liddicoat et al. |
| 2010/0069925 A1 | 3/2010 | Friedman et al. |

* cited by examiner

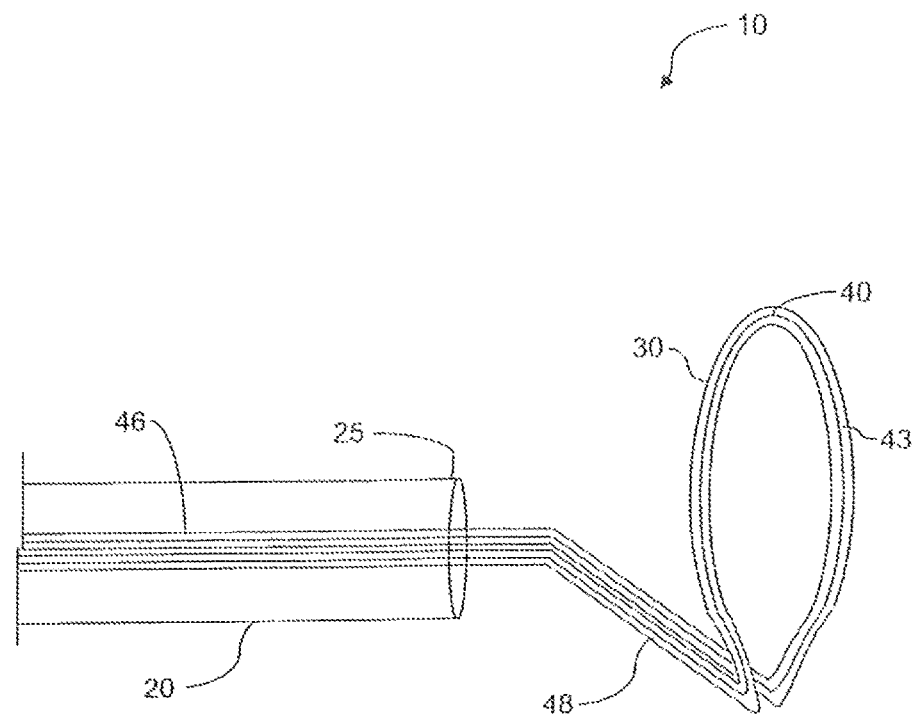

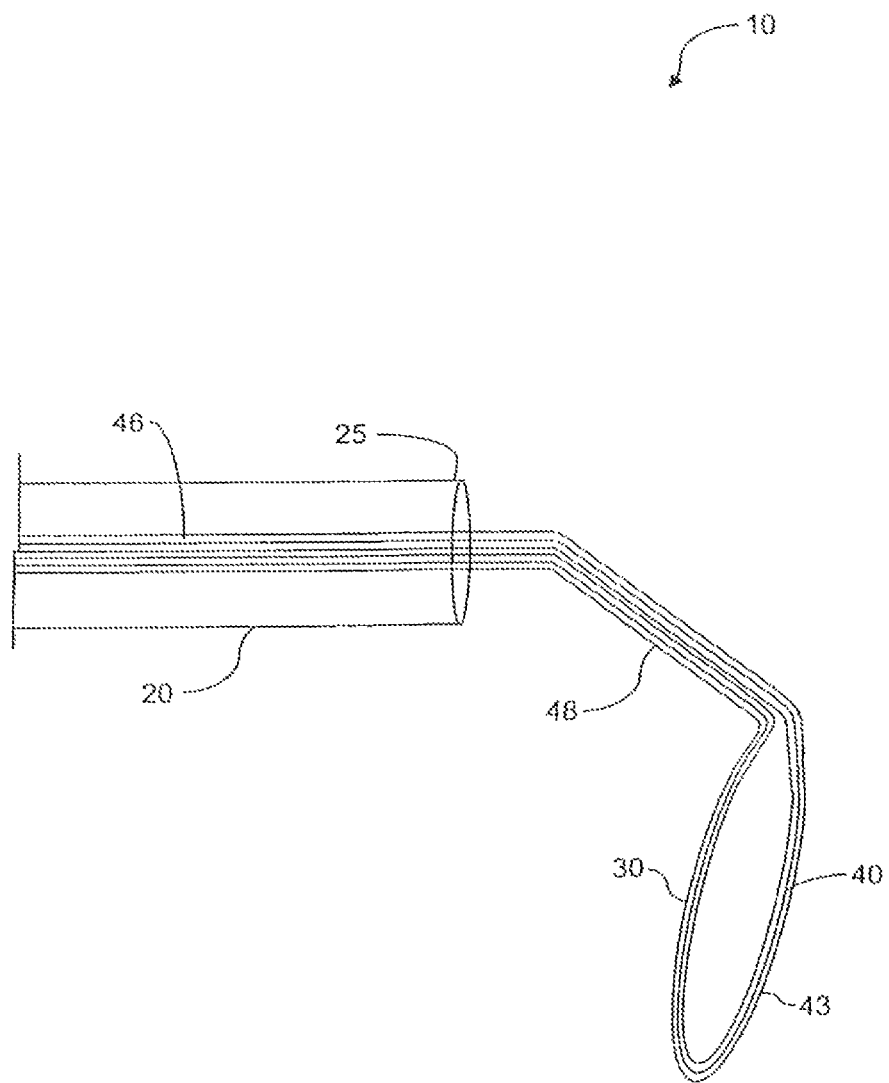

DEVICES AND METHODS FOR LIGATING ANATOMICAL STRUCTURES

RELATED APPLICATIONS

This application is a continuation application of U.S. patent application Ser. No. 12/442,294 filed on Oct. 28, 2009, which is a U.S. National Stage Application of International Application No. PCT/US2007/020509, filed on Sep. 21, 2007, which claims the benefit of U.S. Provisional Patent Application Ser. No. 60/826,413 filed on Sep. 21, 2006 and titled DEVICES AND METHODS FOR LIGATING ANATOMICAL STRUCTURES, all of which are hereby incorporated by reference in their entirety.

The present invention relates to devices and methods for ligating anatomical structures such as, e.g., the left atrial appendage.

Atrial fibrillation is a common cardiac rhythm disorder affecting more than two million people each year, in which the upper part of the heart beats more quickly than the rest of the heart. This phenomenon is due to the generation of erratic or extra electrical signals that cause the top part of the heart to fibrillate rapidly and irregularly. The adult human heart normally beats 60 to 80 times per minute at rest. With atrial fibrillation, the heart can beat as many as 300 to 600 times a minute.

One of the most significant dangers from atrial fibrillation is stroke. In fact, atrial fibrillation can make stroke as much as five times more likely than in the general population. Since the heart does not pump normally or efficiently during atrial fibrillation, blood can pool and stagnate in the atria, resulting in clot formation.

Blood pooling and clot formation is especially likely to occur in the left atrial appendage (LAA). The LAA is a hollow, pedunculated extension that resembles a small windsock formed off the lateral wall of the left atrium. The LAA usually contracts with the rest of the left atrium during normal heart function, thereby continually moving blood throughout the hollow extension. During atrial fibrillation, however, the LAA often fails to contract, thereby allowing blood to pool and stagnate inside the appendage. As a result, thrombus or clot formation can occur. Such clots can be ejected from the LAA into the left atrium and left ventricle, and then can be released into the bloodstream to become potential obstructions in the brain or in other vascular structures.

SUMMARY

The present invention provides methods and devices for ligating anatomical structures, where anatomical structures include both those that are purely anatomical and those that are pathological. In some instances, the structures are ligated to, e.g., reduce or prevent blood clot formation in and release from a structure such as the LAA. These methods and devices can be used to ligate the LAA, thus preventing blood from entering the appendage, pooling, and forming clots. Ligation of the LAA also can prevent or reduce the escape of previously formed clots into the bloodstream. The methods and devices provided herein can facilitate minimally invasive treatment for atrial fibrillation. These methods can be performed in conjunction with other procedures (e.g., mitral valve replacement, radiofrequency ablation, atrial fibrillation ablation, coronary artery bypass, etc.) or they can be performed solely to ligate the anatomical structure (such as the LAA).

Although the exemplary devices and methods described herein focus on ligation of the LAA, the devices and methods of the present invention can be useful for ligation of other anatomical structures, including, e.g., the gallbladder, the GI appendage, diverticuli, fallopian tubes or ovaries, vascular aneurysms, or any other pedunculated structure or mass. The devices can be used in any laparoscopic or minimally invasive surgery in which it would be useful to ligate, tie, or clip a structure via a single port access.

In one aspect, the present invention provides a ligating device that includes a catheter having a proximal end and a distal end; a ligating element located within the catheter, wherein the ligating element includes a lumen and a first end and a second end, wherein the first end and the second protrude from the proximal end of the catheter; and a control element located within the lumen of the ligating element, the control element including a first end that protrudes from the first end of the ligating element, wherein a distal portion of the control element forms an open loop upon exit from the distal end of the catheter, and wherein the open loop is compressed when the distal portion of the control element is located within the catheter, and further wherein the control element forces the ligating element to adopt a lariat configuration when outside of the catheter.

In various embodiments, the ligating devices described herein may include one or more of the following features: the control element may be removable, such that the control element can be pulled out of the lumen of the ligating element; the control element may include a second end that protrudes from the ligating element; a portion of the ligating element may include a knot formed therein; the control element may extends through the portion of the ligating element that includes a knot; and the control element may include a distal portion and a proximal portion, and the distal portion may be thinner than the proximal portion; the ligating element may be a hollow suture and the control element may include shape memory material; the lariat may be formed at an angle with respect to an elongate portion of the control element from which the lariat extends; the control element may include an angled portion when the control element is located outside of the catheter; a positioning element may be attached to the lariat of the ligating element; the ligating device may include an appendage positioning element; the control element may include magnetizable material such that the position of the ligating element can be manipulated by a magnetic device; and a sheath may be provided in which the catheter is located; etc.

In still other embodiments, the ligating devices may include one or more of the following features: the ligating element may include a knot formed therein and the control element may have a distal end that is located distal from the knot; a secondary control element may be located within a portion of the ligating element, wherein a distal end of the second control element may be located proximal from the knot such that the second control element does not extend through the knot; etc.

In another aspect, the present invention may provide a ligating device that includes a catheter having a proximal end and a distal end; an elongate element located within the catheter, the elongate element having a proximal end and a distal end; a ligating element located within the catheter, wherein the ligating element is attached to the distal end of the elongate element, and further wherein the ligating element comprises an original shape of a closed loop; a control element located within the catheter, the control element including a first end that protrudes from the proximal end of the catheter, wherein a portion of the control element is contained within the ligating element, wherein pulling on the first end of the control element opens the ligating element from its original closed loop shape to open the ligating element into a lariat configuration. The ligating element may be rotatably attached to the elongate element.

In another aspect, the present invention may provide a ligating device that includes a catheter having a proximal end and a distal end; an elongate element located within the catheter, the elongate element having a proximal end and a distal end; a ligating element located within the catheter, wherein the ligating element is attached to the distal end of the elongate element, and further wherein the ligating element includes a ring clip whose natural position is closed; a hollow control element attached to the ligating element; and a conduit in fluid communication with the hollow control element, wherein the conduit extends to the proximal end of the catheter, wherein pressurized fluid delivered to the control element inflates the control element to open the ligating element. The ligating device may further include one or more of the following features: the control element may be located inside or outside of the ligating element; the conduit may be located within the elongate element; a source of pressurized fluid may be in fluid communication with the conduit; etc.

In another aspect, the present invention may provide a ligating device that includes a catheter having a proximal end and a distal end; a control element located within the catheter, wherein the control element has an elongate U-shape with both ends protruding from the proximal end of the catheter and the bottom of the U-shape positioned near the distal end of the catheter; and a ligating element attached to one end of the control element; wherein the end of the control element that is not attached to the ligating element can be pulled to advance the ligating element through the catheter. The ligating device may include a tubular sheath surrounding a portion of the control element at the distal end of the catheter, wherein advancing the ligating element also advances the ligating element through the tubular sheath.

In another aspect, the present invention provides a ligating device that includes a catheter having a proximal end and a distal end; a control element located within the catheter, the control element having a first elongate portion located within the catheter, the first elongate portion including a proximal end and a distal end, wherein the control element further includes a second elongate portion located within the catheter, the second elongate portion having a proximal end and a distal end; and a ligating element attached to the distal ends of the first elongate portion and the second elongate portion, wherein manipulation of the first elongate portion and the second elongate portion cause the ligating element to form a lariat.

In another aspect, the present invention provides a method of ligating an anatomical structure that includes advancing a ligating device as described herein to a selected anatomical structure; and operating the ligating device to ligate the selected anatomical structure.

In another aspect, the present invention provides a tissue piercing device that includes a hollow sheath; and a wire disposed within the hollow sheath, wherein the wire includes a distal end configured to coil after being deployed out of the sheath. The tissue piercing device may further include a hollow needle contained within the hollow sheath, wherein the wire is disposed within the hollow needle.

In another aspect, the present invention provides a tissue piercing device that includes a hollow sheath; and a wire disposed within the hollow needle, wherein the wire includes an RF tip at its distal end. The tissue piercing device may further include a hollow needle contained within the hollow sheath, wherein the wire is disposed within the hollow needle.

In another aspect, the present invention can provide a device that includes a hollow flexible catheter having a proximal end and a distal end; an elongate ligating element disposed within the catheter, wherein the ligating element has a first end and a second end that protrude from the proximal end of the catheter; and an elongate control element disposed within the ligating element, wherein the control element has a first end and a second end that are positioned toward the proximal end of the catheter, wherein at least one of the first and second ends of the control element protrudes from an end of the ligating element, wherein the control element comprises shape memory material, and wherein at least a portion of the control element is shaped to form an open loop upon exit from the distal end of the catheter.

The ligating element can be in the form of a hollow suture. The suture can include materials such as, e.g., PTFE, polyethylene, or polypropylene. The control element can include shape memory materials such as, e.g., Nitinol. The loop formed by the control element can be at an angle with respect to another portion of the control element. The control element can further form an angled section upon exit from the distal end of the catheter. The device can potentially have a length between about 12 inches and about 60 inches (e.g., between about 36 inches and about 48 inches). The device can potentially have a diameter between about 0.05 cm and about 3 cm (e.g., between about 0.1 cm and about 0.4 cm). The device can further include a positioning element disposed within the catheter, a sheath in which the catheter is disposed, and/or an appendage positioning element.

In another aspect, the present invention can provide a device that includes a hollow flexible catheter having a proximal end and a distal end; an elongate element disposed within the catheter, wherein the elongate element has a proximal end extending from the proximal end of the catheter and distal end positioned near the distal end of the catheter; a rigid ligating element attached to the distal end of the elongate element, wherein the ligating element includes shape memory material configured in a closed loop; and a flexible control element disposed within the catheter and contained within at least a portion of the ligating element, wherein the control element has a first end and a second end, wherein at least one of the first and second ends of the control element protrudes from the proximal end of the catheter.

The ligating element can include a shape memory material such as, e.g., Nitinol. The ligating element can be rotatably attached to the elongate element. The ligating element and the elongate element can be attached via a pin, about which the ligating element can rotate with respect to the elongate element. The ligating element can include atraumatic material (e.g., PTFE or DACRON™). The control element can include, e.g., a suture, a string, a flexible wire, etc. The device can, e.g., have a length between about 12 inches and about 60 inches (e.g., between about 36 inches and about 48 inches). The device can, e.g., have a diameter between about 0.05 cm and about 3 cm (e.g., between about 0.1 cm and about 0.4 cm). The device can further include a positioning element disposed within the catheter, a sheath in which the catheter is disposed, and/or an appendage positioning element.

In another aspect, the present invention may provide a device that includes a hollow flexible catheter having a proximal end and a distal end; an elongate element disposed within the catheter, wherein the elongate element has a proximal end extending from the proximal end of the catheter and a distal end positioned near the distal end of the catheter; a flexible, hollow, donut-shaped control element attached to the distal end of the elongate element, wherein the control element has an outer surface and an inner lumen; and a rigid ligating element contained within or positioned around the ligating element, wherein the ligating element includes shape memory material and is in the form of a closed loop.

The elongate element can define a lumen between the proximal and distal ends, and wherein the lumen of the elongate element is in fluid communication with the lumen of the control element. The control element can include, e.g., PTFE, polyethylene, or polypropylene. The ligating element can include shape memory materials such as, e.g., Nitinol. The device can, e.g., have a length between about 12 inches and about 60 inches (e.g., between about 36 inches and about 48 inches). The device can, e.g., have a diameter between about 0.05 cm and about 3 cm (e.g., between about 0.1 can and about 0.4 cm). The device can further include a positioning element disposed within the catheter, a sheath in which the catheter is disposed, and/or an appendage positioning element.

In still another aspect, the present invention may provide a device that includes an elongate, hollow, flexible sheath having a tapered distal end; an elongate, hollow needle disposed within the sheath; and an elongate wire disposed within the needle. The wire can have a distal end, and may include a radiofrequency electrode at the distal end. The hollow needle can have a curved distal end. The device can further include means for advancing a portion of the wire out of the distal end of the sheath. The wire can have a distal end configured to coil after being advanced out of the distal end of the sheath.

The present invention may also provide a method for accessing the pericardial space of a subject. The method can include passing a device as described herein through the circulatory system and into the left coronary sinus of the subject; and piercing the wall of the coronary sinus or coronary venous system of the subject to access the pericardial space.

In another aspect, the present invention may provide a method for ligating the left atrial appendage in a subject. The method can include advancing the distal end of a ligation device as described herein into the chest of the subject; placing the distal end of the device within the pericardium of the subject; and positioning the ligating element around the base of the left atrial appendage. The distal end can be advanced into the chest of the subject via a suprasternal, intercostal, or sub-xiphoid approach. The distal end can also be advanced through the coronary sinus or one of its tributaries into the pericardial space.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The words "preferred" and "preferably" as used herein refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a ligating element can include one or more ligating elements The term "and/or" means one or all of the listed elements or a combination of any two or more of the listed elements.

The details of one or more embodiments of the invention are set forth in the accompanying drawings and the description below. Other features and advantages of the invention will be apparent from the description and drawings, and from the claims.

BRIEF DESCRIPTIONS OF THE DRAWINGS

FIGS. 4A and 4B are cross-sectional/perspective views of the distal portion of devices having a lariat or loop oriented at an angle relative to the elongate portion of the ligating and control elements, and further having an elongate element with an angled portion.

Like reference symbols in the various drawings indicate like elements.

DESCRIPTION OF EXEMPLARY EMBODIMENTS OF THE INVENTION

Figure 1:
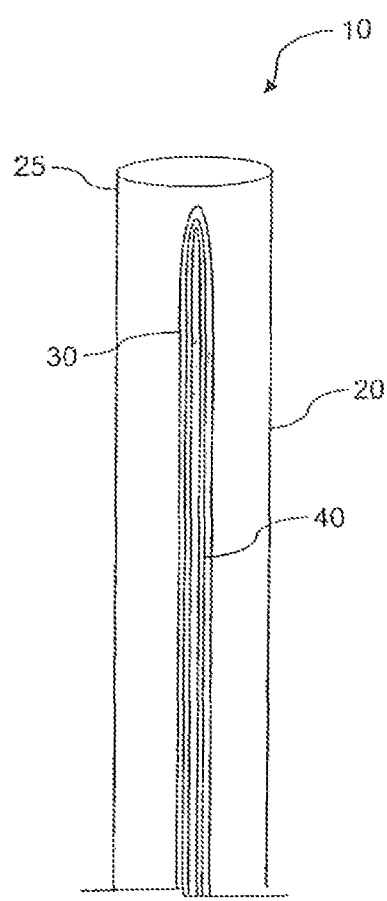
FIG. 1 is a cross-sectional view of the distal portion of a ligating device having a catheter with a hollow suture ligating element and a control element contained within the hollow suture ligating element, where the ligating and control elements are in a closed configuration.

The devices and methods provided in connection with the present invention can be used to ligate anatomical structures such as, e.g., the LAA and other anatomical features. Although the exemplary embodiments described herein are discussed in the context of LAA ligation, the devices and methods of the present invention should not be limited to that use. Ligation of anatomical structures may be performed for a variety of reasons. Ligation of the LAA may, for example, reduce the likelihood of or prevent clots from forming in the LAA and/or reduce the likelihood of or prevent previously formed clots from escaping into the bloodstream.

In general, the ligating devices of the present invention may include a ligating element and a control element. The control element can be contained within the ligating element or the ligating element can be contained within the control element. In other embodiments, the ligating element can be separate from the control element. For example, the ligating element can encircle the control element, or vice versa, or an end of the ligating element (e.g., a length of suture) can be attached to an end of the control element (e.g., a length of wire), such that neither element is contained within the other.

The ligating element, the control element, or both the ligating element and the control element can be contained within the lumen of a catheter having proximal and distal ends, with the lumen defined therebetween. At least a portion of the ligating element and/or at least a portion of the control element can be positioned at the distal end of the catheter. In some embodiments, the ligating element and/or the control element can extend through the length of the catheter. In other embodiments, the ligating element and/or the control element can be positioned at the end (e.g., the distal end) of a separate elongate element, such that the elongate element extends through the length of the catheter and the ligating and/or control elements are positioned at the distal end of the catheter. For example, in some cases the ligating element can be positioned at the distal end of an elongate element within the catheter, and the control element can extend through all or a portion of the ligating element and through the length of the catheter.

The ligating element can be adapted for placement around the LAA (e.g., the base of the LAA) or other anatomical structure, such that the LAA can be effectively closed off from the left atrium. The control element can be adapted to facilitate placement of the ligating element in the desired position around the LAA. Typically, at least one of the ligating element or the control element can be constructed to be rigid and/or to have shape memory, such that the ligating element and/or control element can have a closed configuration for passage through the catheter and eventual tightening around the base of the LAA, and an open "lariat" configuration for placement over and around the body of the LAA.

The lariat formed by the ligating element and/or control element in the open configuration can have any suitable shape and size. For example, a lariat can have an essentially circular or oval shape, or can have an irregular shape to, for example, follow the curve of the heart. A lariat can have a maximum diameter from, e.g., about 0.5 cm to about 4 cm (e.g., from about 0.7 cm to about 3.5 cm, from about 1.0 cm to about 2.5 cm, or from about 1.5 cm to about 2.0 cm).

The ligating devices provided in connection with the present invention may be readily deployed in a percutaneous manner. In addition, the ligating devices can be adapted to minimize trauma to the tissue they contact such that there is little or no erosion through the tissue, reducing the likelihood of bleeding and cardiac tamponade. Further, the devices can be reversible and/or repositionable, such that a clinician can position the ligating element over the LAA, tighten the ligating element around the LAA, and then loosen and reposition the ligating element if desired.

In some embodiments, a ligating device can have a hollow ligating element formed of a soft, pliable material (e.g., polytetrafluoroethylene (PTFE), polyethylene, polypropylene, or any other suitable material), and an inner control element formed of a more rigid material (e.g., wire, etc.) or any other suitable material that can provide the hollow element with at least temporary rigidity (e.g., pressurized fluid such as water or air).

For example, a ligating element can be in the form of a hollow (e.g., PTFE) suture, with a control element running through the lumen of the hollow suture. The wire loaded suture can have a generally elongate "U" shape and can extend through the length of the catheter, with both ends protruding from the proximal end of the catheter and the bottom of the "U" positioned at or near the distal end of the catheter. The distal end of the device can be positioned near the LAA (or other anatomical structure) via any suitable approach (e.g., via sub-xyphoid, intercostal, or trans-coronary sinus approach for the LAA). The ligating element can be passed through the distal end of the catheter and placed around the base of the LAA.

In some embodiments, the inner control element can be made of a shape memory material (e.g., Nitinol), such that when the hollow ligating element exits the distal end of the catheter it assumes an open "lariat" configuration to facilitate placement around the LAA or other anatomical structure. The inner control element may also give the ligating element a configuration that places (orients) the lariat at an angle with respect to the elongate portion of the ligating element, to further facilitate positioning of the device over the LAA or other anatomical structure. In some embodiments, the control element can be configured such that as the ligating element is progressively extended out of the distal end of the catheter, the shape and angulation of the lariat changes. The angulation and shape of the ligating device can, in some embodiments, be tailored based on patient anatomy. Angled configurations of the control element can provide additional control of the lariat, to further facilitate positioning of the device.

In addition, a ligating device provided in connection with the present invention may include a separate positioning element, which also can be used to position and reposition or remove the ligating element if desired. A clinician also can manipulate either or both ends of the inner control element to alter the shape and/or position of the ligating element. In some embodiments, the control element can contain a magnetizable material (e.g., iron, nickel, cobalt, gadolinium, dysprosium, or composites of flexible resins and magnetic powders, with or without a binder such as vinyl), and the position of the ligating element can be manipulated by a magnetic device outside the body (e.g., a magnetic navigation system from, for example, Stereotaxis, Inc. of St. Louis, Mo.).

Once placed, the ligating element can be retained in position via a clip or any other suitable means. The control element can be removed if desired (e.g., by pulling on one end of the control element such that it slides out of the lumen in the ligating element). Once the control element is removed, the ligating element can be tightened to close the LAA and then fixed in position via a clip, a knot, or any other suitable fastening means.

If a knot is used, the knot can be tied outside the body and pushed through the catheter into position to close the LAA. Examples of suitable knot pushing devices and methods are described in, for example, U.S. Pat. Nos. 6,132,439, 5,759,189, and 5,769,863. A knot pushing device can be made from a substantially rigid material, from a flexible material (e.g., polypropylene or polyethylene), or from a combination of flexible and rigid materials.

In some embodiments, a ligating device of the present invention can have a ligating element formed of a rigid material (e.g., shape memory material such as Nitinol, etc.), and an inner or outer control element formed of a pliable material (e.g., suture, soft wire, or any other suitable material). The ligating element can be positioned at the end of an elongate element that extends through the length of the catheter, such that the ligating element can be positioned at or toward the distal end of the device, within the lumen of the catheter.

The rigid (e.g., shape memory) material of the ligating element can be covered on its exterior surface with a coating (e.g., PTFE, DACRON™, or other suitable material) to, for example, prevent tissue trauma. Examples of suitable coatings are described elsewhere (e.g., U.S. Publication No. 2005/0277959).

In some cases, the natural position or configuration of the ligating element can be closed. Such a position or configuration can facilitate passage of the ligating and control elements through the catheter, and can provide a ready means to close off the LAA after placement of the ligating element.

An inner control element can extend through the entire length of the ligating element or through a portion of the ligating element. An outer control element can extend around (e.g., encircle) the entire ligating element, or can be attached to a portion of the ligating element. In some embodiments, a control element can be secured at or near the distal end of the ligating element.

In use, a clinician can pull on the control element in the proximal direction, opening the ligating element into a lariat configuration to allow for positioning of the device over the LAA. In some cases, an inner control element extending through the entire length of a ligating element may not be secured within the ligating element, but can be configured such that a clinician can apply force in the proximal direction (e.g., by pulling on both ends of the control element) to open the ligating element. The ligating element can have a pre-formed shape that, for example, facilitates opening of the lariat upon actuation of the control element. For example, a ligating element containing a shape-memory material can have a preformed shape with preferential bends to facilitate formation of a lariat.

In some cases, a portion of the ligating element (e.g., at a point on the base of one side of the ligating element) can be affixed to the distal end of the catheter or the sheath. In these cases, the control element can be actuated (e.g., pulled in the proximal direction) such that the unaffixed side of the ligating element can move into the catheter, causing the affixed side to bend, thus forming a loop. In some embodiments in which a portion of the ligating element is affixed to the distal end of the catheter, the unaffixed side of the ligating element can be magnetized. In such embodiments, a clinician can use a magnet or magnetic system outside the subject's body to manipulate the ligating element and pull the unaffixed, magnetized side of the ligating element into the catheter, thus causing the ligating element to form a lariat. In some cases in which a portion of the ligating element is magnetized, a device may lack a separate control element.

Once the ligating element is in position, the control element can be released to close the ligating element. The ligating element can be separated from the elongate element and, in some cases, from all or a portion of the control element. Any suitable means can be used to separate the ligating element from other elements of the device. An inner control element can be left entirely or partially inside the ligating element. An outer control element can be entirely or partially removed from the ligating element.

In some embodiments, a rigid ligating element can be connected to an elongate element by a pin or other mechanism at its base to, for example, allow a clinician to adjust the angle of the ligating element with respect to the elongate element (e.g., once the ligating element has been advanced beyond the distal end of the catheter). The ability to manipulate the angle of the ligating element can facilitate positioning of the ligating element over the LAA.

In some embodiments, a device can include a ligating element in the form of a ring clip (e.g., manufactured of shape memory wire) whose natural position is closed, and a hollow, donut-shaped control element comprising a soft pliable material (e.g., PTFE, polyethylene, or polypropylene) that is air tight. In some embodiments, the ring clip can be contained within the control element. For example, a ring clip (formed of, e.g., Nitinol) can be contained within a hollow ring (of, e.g., PTFE). In some cases, the ring clip can encircle the outer circumference of the control element. For example, a ring clip (formed of, e.g., Nitinol) can encircle a hollow ring (of, e.g., PTFE). The device can be deployed by advancing the ligating element (ring clip) and the control element out of the distal end of the catheter, inflating the control element (e.g., with a gas or a liquid) to open the ring clip, positioning the device at the base of the LAA, and deflating the control element to close the ring clip. In such embodiments, the control element can provide an atraumatic covering for the ligating element.

In some embodiments, a device can have an elongate rigid control element (e.g., a wire) with a ligating element (e.g., a suture) affixed to one end. The control element can extend through the length of the catheter, e.g., with a generally elongate "U" shape in which both ends protrude from the proximal end of the catheter and the bottom of the "U" is positioned at or near the distal end of the catheter. A clinician can manipulate the position of the control element using, for example, a positioning element as described herein, or using a magnet in cases where the control element is magnetized. Once the control element is placed around the LAA, the end of the control element that is not attached to the ligating element can be pulled to advance the ligating element through the catheter and around the LAA. When the ligating element is in place around the base of the LAA, it can be fastened in place (e.g., knotted or clipped), and any remaining portion of the ligating element and the control element can be retracted from the subject's body.

In some cases, the ligating device can include a protective element. For example, the ligating device can include a hollow tubular sheath that can surround a portion of the control element at the distal end of the catheter, and can be placed around the LAA (or other anatomical structure) along with the control element. Such a sheath can protect the tissue from frictional damage as the control element is pulled through the catheter and the suture is positioned around the LAA (or other anatomical structure). A protective element also can distribute the force of the suture over a greater area of the LAA.

In some embodiments, a ligating device of the present invention can include a control element having two rigid elongate portions (e.g., two lengths of wire extending through the catheter) with a flexible ligating element attached to the ends of the control element closest to the distal end of the catheter. By manipulating the elongate portions of the control element with respect to one another, a clinician can cause the flexible ligating element to form a lariat that can be placed around the LAA (or other anatomical structure). A fastening means (e.g., a clip) can be passed through the catheter (e.g., along one or both portions of the control element) to retain the ligating element around the base of the LAA. Once the lariat is in place, a clinician can cut any excess portion of the ligating element, and remove the device from the subject's body.

Ligating devices of the present invention can include one or more additional elements to assist with positioning of the ligating element and/or the LAA (or other anatomical structure). These additional elements can, e.g., be contained within the catheter or within an outer sheath that also contains the catheter. Positioning elements can be deflecting and/or steerable to, for example, facilitate their positioning within a device.

Appendage positioning elements can include, for example, suction catheters, forceps, and cryogenic-tipped catheters, which can be used to lift and hold the LAA while the lariat is put into position at its base. See, e.g., U.S. Patent Application Publication Nos. 2005/0154404 and 2004/0030335, as well as U.S. Pat. No. 6,488,689. An appendage control device can be, for example, a suction device, a grasper device, or a cryogenic device. A suction device can lift and/or hold the LAA by applying a gentle vacuum to the surface of the LAA, while a grasping device can physically hold the LAA. A cryogenic appendage control device can be, for example, a probe with a cooled tip that can attach to the LAA like a tongue to a cold flag pole, and that can be warmed to permit removal from the surface of the LAA with minimal trauma to the tissue.

In addition or alternatively, a positioning element can be used to help position and place the ligating element. A positioning element can be rigid or at least substantially rigid, as in the case of a rod comprising wire, plastic, or any other suitable material. Alternatively, a positioning element can be flexible, as in the case of a suture having a loop through the lariat. In some cases, a positioning element can be releasably attached to the lariat via any suitable means (e.g., threads, a pin, or a magnet), or can include a hook at one end for grasping the lariat. The positioning element can be used to push, pull, or otherwise maneuver the lariat into position, and can remove the positioning element from the lariat once the device is positioned around the LAA. In some embodiments, a first lariat can be positioned around the LAA, and then can be used as a positioning and/or control element to facilitate placement of a second lariat around the base of the LAA.

The ligating devices provided herein can have any suitable length and width (e.&, diameter). For example, a device can have a length between about 12 inches and about 72 inches (e.g., between about 24 inches and 60 inches, between about 30 inches and about 54 inches, or between about 36 inches and about 48 inches), such that its distal end can be placed within the pericardial space proximate the LAA and its proximal end can be positioned outside a subject's body. Further, a device can have any suitable diameter. For example, a device can have an overall diameter (e.g., diameter of the outer sheath, or diameter of the catheter if there is no outer sheath) suitable for passage through the circulatory system and into the coronary sinus, for passage between adjacent ribs, or for sub-xiphoid passage. Thus, a device can have a diameter between about 0.05 cm and about 1.5 cm, between about 0.1 cm and about 1.0 cm, between about 0.15 cm and about 0.5 cm, between about 0.2 cm and about 0.4 cm, or about 0.2 cm, about 0.3 cm, or about 0.4 cm. The device may be flexible to permit navigation through curved and finite planes (such as the pericardial space) leading to the anatomical structure (such as the LAA).

The ligating devices provided herein can be used in any suitable type of minimally invasive approach. In some embodiments, a ligating device can be used in an intercostal approach. For example, a mini-thoracotomy procedure can be used in which the distal end of a device can be inserted through a small incision into the chest cavity and advanced between the ribs to the pericardium. In some embodiments, a sub-xiphoid approach can be used, in which the distal end of a device is inserted into the chest cavity through a small incision and advanced between the xiphoid process and adjacent intercostal cartilage until it reaches the pericardium. In some cases, a suprasternal approach can be used, in which the distal end of a device is inserted into the chest cavity through a small incision above the sternum, and advanced inferiorly toward the pericardium. For intracostal, sub-xiphoid, and suprasternal approaches, the distal end of a device can be advanced into the pericardial space through the pericardium (i.e., from the exterior of the pericardium), and positioned at or near the LAA.

In some embodiments, controlled exit from the coronary sinus (CS) can be used. CS exit can be advantageous in that the angle of approach can facilitate encircling the LAA at its base. In this approach, a device (e.g., a tapered, flexible sheath or catheter) can be passed into the coronary sinus via, for example, a femoral vein, a jugular vein, or a subclavian vein. The sheath can have a hollow needle and/or a wire contained therein when it is passed into the CS, or a needle and/or wire can be passed through the sheath after it reaches the CS. The tip of the device can be positioned within the CS, and the distal end of the needle or wire can be advanced through the wall of the CS and into the pericardial space proximate the LAA. In some embodiments, the distal end of the sheath or needle can be curved or angled, such that a wire contained therein is directed to exit the needle toward the CS wall rather than into the lumen of the CS. A similar approach discussed herein could potentially be used to facilitate a controlled exit from the right atrial appendage.

A device can include any suitable mechanism to facilitating piercing of the CS wall. For example, the needle can contain a wire that can be "cocked" with a spring mechanism. A clinician can actuate the spring mechanism, and the resulting forward pressure applied on the wire element can cause the needle or the wire within the needle to pierce the CS wall. In some embodiments, the wire can be configured such that once it enters the pericardial space, it can curve and/or kink to prevent further advance of the needle beyond the pericardial space. For example, a wire can be configured to coil after piercing the CS wall, thus reducing the likelihood of or preventing the end of the wire from puncturing the pericardial sac or damaging the outer surface of the heart. In some cases, a device can be configured such that the length of wire deployed from the device is limited. For example, the length of wire that exits the catheter or needle is limited to between about 0.5 mm and about 3 mm (e.g., about 0.5 mm, about 1 mm, about 1.5 mm, about 2 mm, about 2.5 mm, or about 3 mm).

In some embodiments, a wire can have a RF electrode at its tip. Thus, RF energy can be used to create an opening in the CS wall for passage of the needle or catheter. The RF energy can be turned off once the CS wall is pierced, to prevent puncture of the pericardial sac. The sheath and/or the hollow needle can have an angled or curved end, which can facilitate placement advancement of the wire toward and through the CS wall.

Once the CS wall is pierced, the device (e.g., the sheath, the needle, or the wire) can be advanced into the pericardial space. The wire and, in some embodiments, the needle, can be removed from the sheath, and a ligating device as described herein can be passed through the sheath and advanced into the pericardial space. In some embodiments, a RF ablation electrode can be passed along or over the wire and into the pericardial space, and can be used for pericardial mapping and/or ablation. A sheath and/or a hollow needle having an angled or curved end can facilitate placement of a ligating device or a RF electrode within the pericardial space.

In some embodiments, a device can include a balloon that can be deployed within the CS to prevent or reduce blood leakage into the pericardial space, and/or to stabilize the device. The balloon can be connected to a fluid conduit that extends through the sheath, and through which a fluid such as air, oxygen, water, or saline can be passed into the balloon. The balloon can be inflated when the device is positioned within the CS, and can be deflated prior to removal of the device from the CS.

After the LAA is ligated, the ligating device can be removed. In some embodiments, the opening in the wall of the CS can be closed. Any suitable technique can be used, including RF ablation or physical closure using one or more hooks and/or needles. For example, a RF-tipped wire can be passed through the sheath or needle to the CS wall, and RF energy can be used to weld the opening. In some cases, tissue at the opening in the CS wall can be pulled into the distal end of the sheath or needle (e.g., using suction or a mechanical grasper), where it can be sutured closed or welded together using RF energy. In some embodiments, a balloon can be passed through the sheath to prevent or reduce blood flow from the CS into the pericardial space.

To use the ligating devices provided herein, in general, a clinician can position the distal end of a device provided herein within the pericardial space proximate the LAA. The device, or a portion thereof (e.g., the catheter) can be steerable using, for example, conventional steerable sheath technology. A clinician can advance the ligating element and control element out of the distal end of the catheter.

A clinician can use the control element and/or a separate positioning rod or suture to position the ligating element around the LAA. In some embodiments, a separate appendage control device as described herein can be used to lift and/or hold the LAA to facilitate suitable placement of the ligating element. Positioning elements can be deflecting and/or steerable. Whether or not a separate control or positioning element is used, once the ligating element is in position, the control element can be removed if desired, and the ligating element can be tightened (around, e.g., the base of the LAA). It is noted that, while in most embodiments the control element and the ligating element are passed through the same device (e.g., the same catheter), control, ligating, and positioning elements can be passed to the LAA through separate devices, such that two or more pericardial access points can be used.

Turning now to the figures, exemplary embodiments of ligating devices in which the ligating element is in the form of a pliable hollow material and the control element comprises a shape-memory wire are depicted in FIGS. 1-10. Device 10 can include catheter 20 with a proximal end (not shown) and distal end 25. Catheter 20 can contain ligating element 30 and control element 40, wherein control element 40 is disposed within the lumen of ligating element 30. In these embodiments, ligating element 30 can be, for example, a hollow suture, and control element 40 can be a wire. Catheter 20 may be placed directly into the pericardial space, or it may enter through a separate sheath already positioned with its distal end in the pericardial space. In addition, the catheter and/or sheath may be steerable. Although the devices are described herein as exiting from the distal ends of the catheters, it should be understood that the exit port through which the devices exit the catheters may be located in the catheter sidewall proximate the distal ends of the catheters or at the very tip of the catheters (as depicted in, e.g., FIG. 2).

Figure 2:
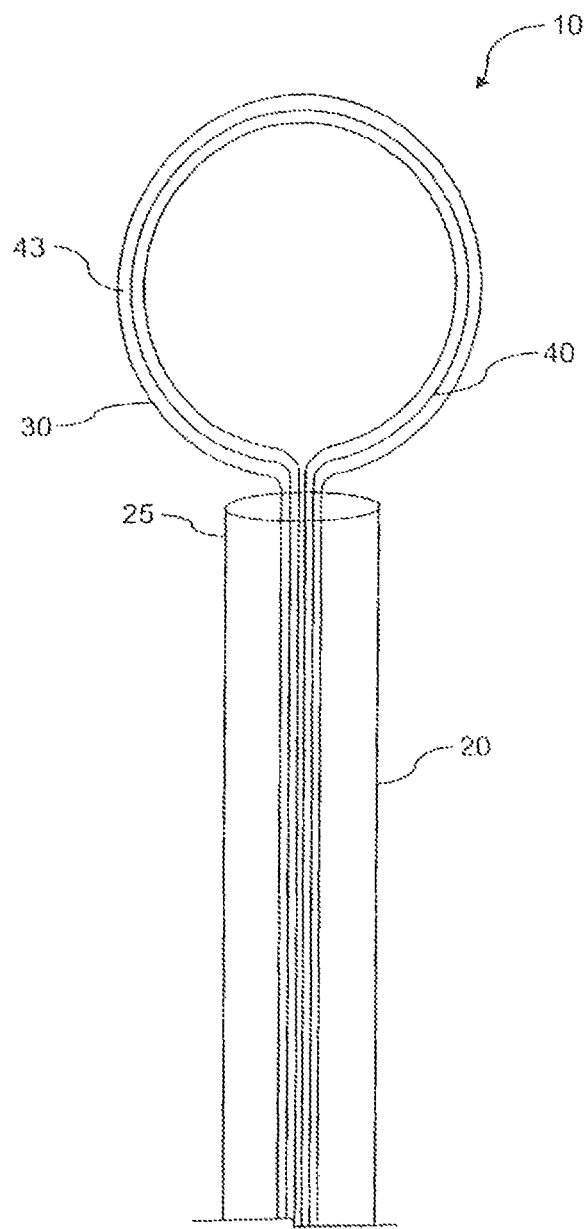
FIG. 2 is a cross-sectional view of the distal portion of the device shown in FIG. 1, wherein the ligating and control elements are in an open configuration, forming a lariat or loop.

Control element 40 can be manufactured of shape-memory material, and can be configured such that, for the portion of control element 40 at distal end 25, the control element has an "original" or "preferred" shape approximating a loop (e.g., a circle or an oval). Thus, when control element 40 is contained within catheter 20 as shown in FIG. 1 (in a closed configuration), it can be compressed into a U-shape that is folded back on itself, but when it is pushed out of distal end 25, it can expand to form lariat 43 as shown in FIG. 2. As such, the loop configuration of control element 40 forces ligating element 30 to adopt a lariat (open) configuration suitable for positioning around, e.g., the LAA. Additionally, preferentially pulling (proximal retraction) on one or the other proximal end of the control elements may modify the shape of the distal loop/lariat to assist with conformation to anatomic variations.

Figure 3:
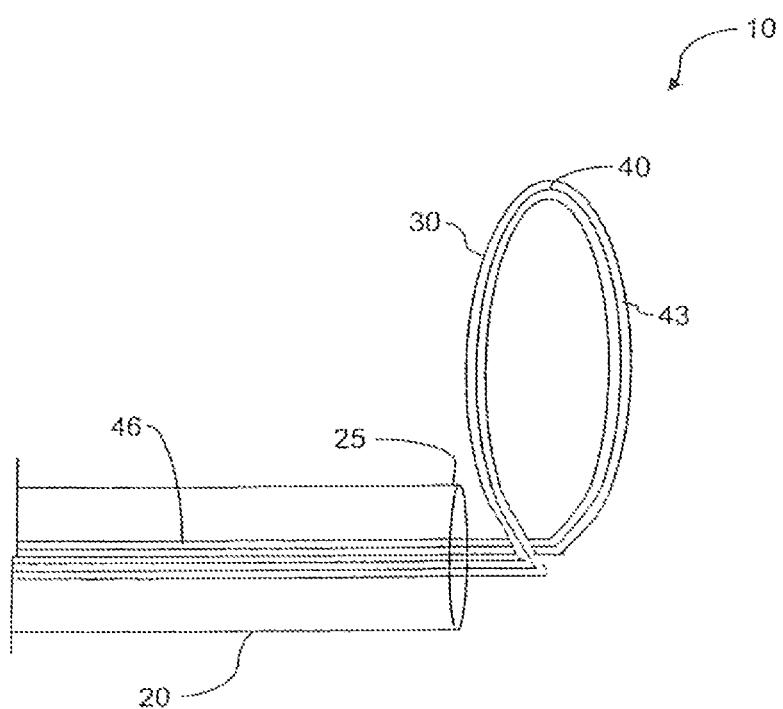
FIG. 3 is a cross-sectional/perspective view of the distal portion of a device having a lariat or loop oriented at an angle relative to the elongate portion of the ligating and control elements.

In some embodiments, control element 40 can be configured such that upon advancement past distal end 25 of the catheter 20, the control element 40 assumes a shape in which lariat 43 is oriented at an angle with respect to the elongate portion 46 of control element 40. For example, as shown in FIG. 3, lariat 43 can be at approximately a 90 degree angle with respect to elongate portion 46 of control element 40. Lariat 43 can be at any suitable angle with respect to elongate portion 46 (e.g., an angle of about 20, 30, 40, 45, 50, 60, 70, 80, 85, 90, 95, 100, 110, 120, 130, 135, 140, 145, or 150 degrees).

In addition or alternatively, the shape assumed by control element 40 can include one or more angled portions, such as angled portion 48 as shown in FIGS. 4A and 4B. Angled portion 48 can further facilitate placement of ligating element 30 around the LAA, and also can facilitate access by an appendage control device (see, e.g., FIG. 6).

Figure 5A:
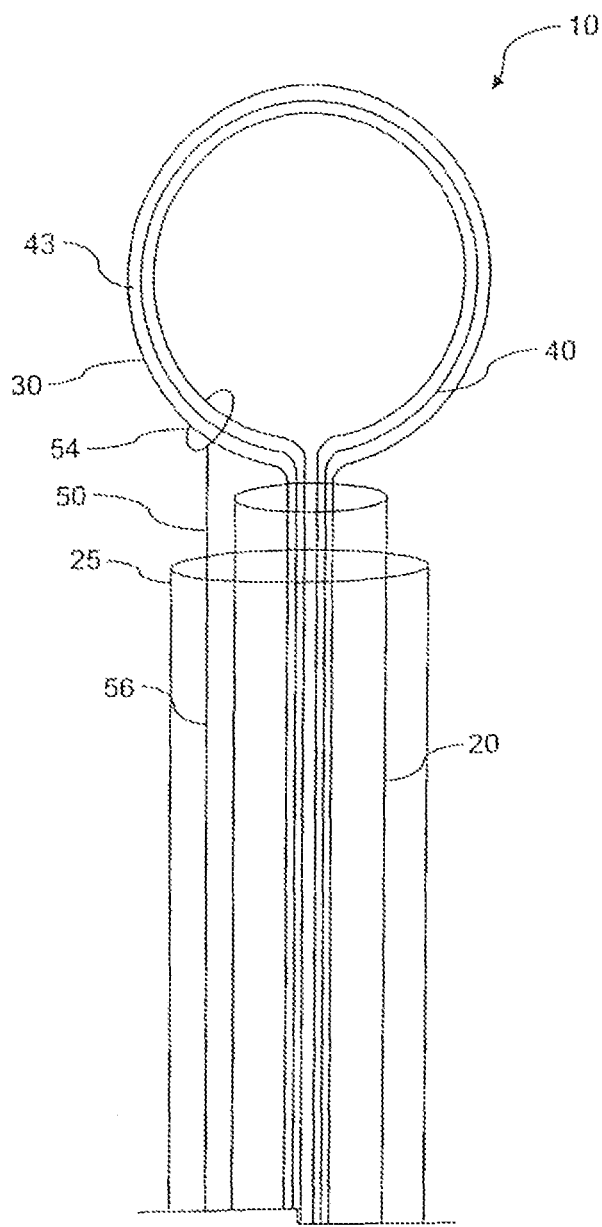
FIGS. 5A and 5B are cross-sectional views of the distal portion of devices having a catheter with a ligating element and a control element contained therein, and further having an outer sheath with a positioning element contained therein. The positioning element is shown at the base of the lariat or loop (FIG. 5A) or at the distal end of the lariat or loop (FIG. 5B).
Figure 5B:
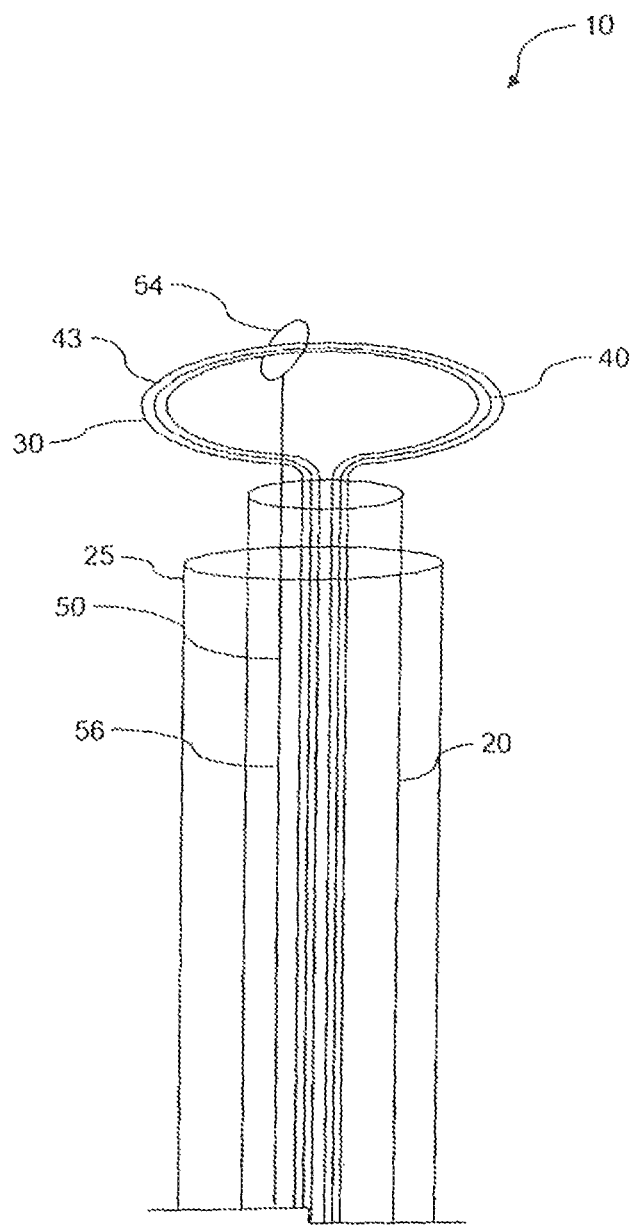

In some embodiments, device 10 can further include positioning element 50, as depicted in FIG. 5. Device 10 also can include outer sheath 60, where catheter 20 and positioning element 50 are contained within outer sheath 60. In some embodiments, positioning element 50 can be contained within catheter 20. Positioning element 50 can include loop 54 and elongate portion 56. Loop 54 can encircle any portion of ligating element 30. For example, loop 54 can encircle ligating element 30 at a position proximate the base of lariat 43, as shown in Figure 5A, or can encircle ligating element 30 at or near the distal end of lariat 43. Elongate portion 56 can extend through the length of outer sheath 60 or catheter 20, such that positioning element 50 can be manipulated outside the body. In use, positioning element 50 can be used to manipulate the position of ligating element 30 (e.g., to deflect lariat 43, as shown in Figure 5B), and thus can facilitate placement of ligating element 30 around the base of the LAA. This element may also potentially be used to loosen a knot after placement and/or facilitate advancement of a cutter through the sheath to remove a loop if, e.g., its position is deemed not favorable.

Figure 6:
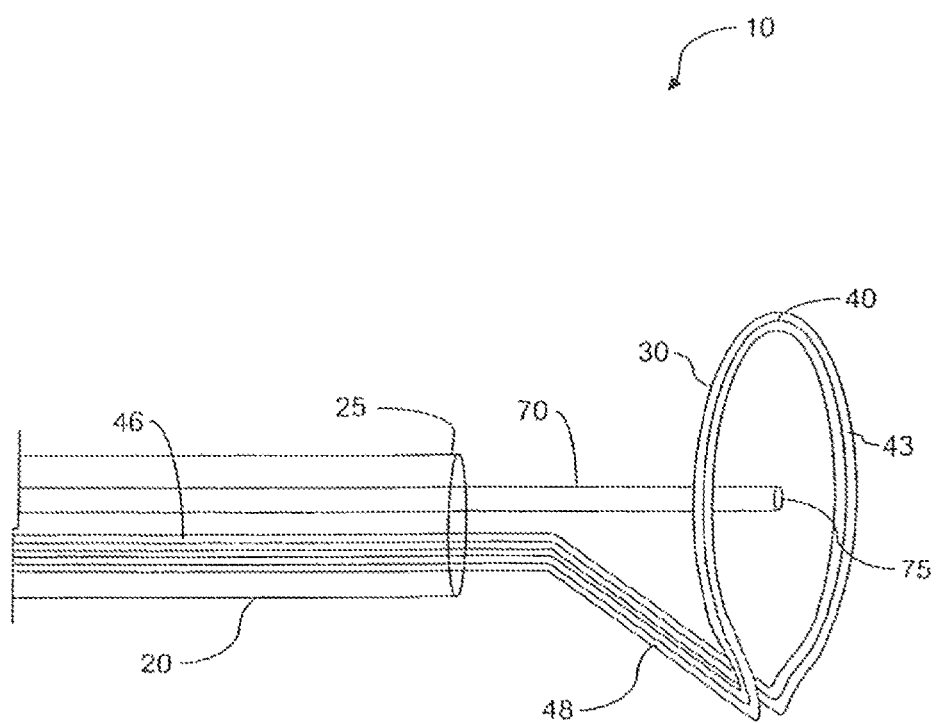
FIG. 6 is a cross-sectional/perspective view of the distal portion of a device as shown in FIG. 3, where the device further includes an appendage positioning device contained within the catheter.
Figure 7:
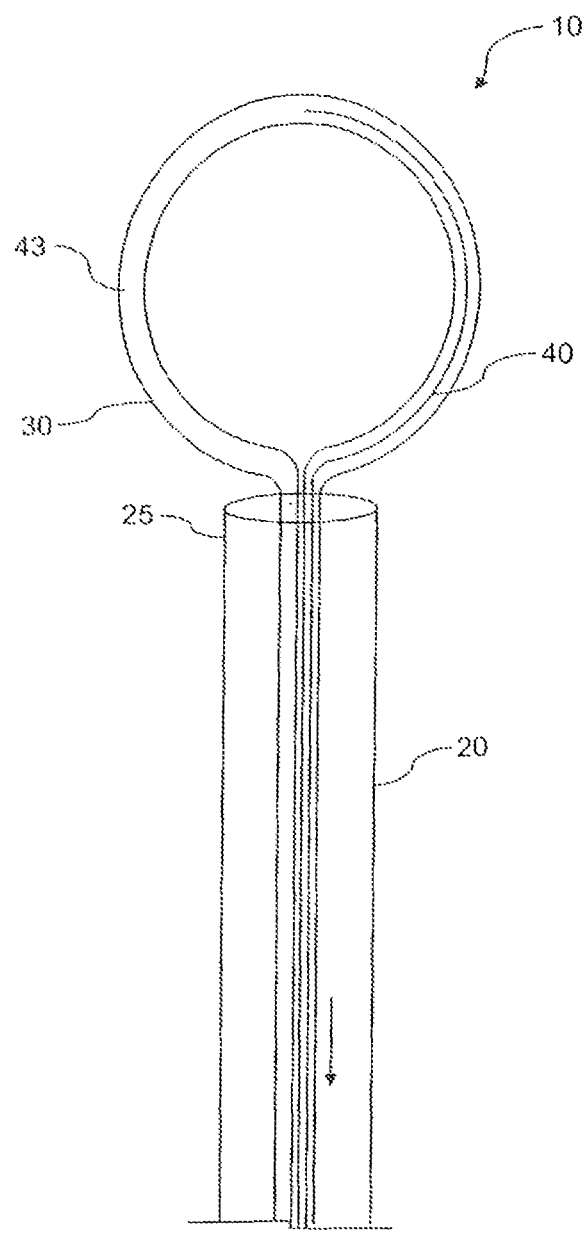
FIG. 7 is a cross-sectional view of the distal portion of the device as shown in FIG. 2, further depicting removal of the control element.

Alternatively or in addition, ligating device 10 can include appendage control means 70. Appendage control means 70 can be contained within the lumen of catheter 20, as shown in FIG. 6, or can be contained within an outer sheath. Appendage control means 70 can extend through the length of catheter 20 or through an outer sheath, and can be in the form of, for example, a suction device, a grasper device, cryogenic device, etc. In use, distal end 75 of appendage control means 70 can be advanced out of catheter 20 and, in some embodiments, through lariat 43, to contact the LAA and hold or lift it into a position suitable for placement of ligating element 30 over the LAA. Once ligating element 30 is placed around the LAA, the LAA can be released from appendage control means 70 by removal of suction if a suction device, by appropriate actuation if a grasper device, or by warming if a cryogenic device. Appendage control means 70 then can be retracted into device 10, or can be advanced to re-grasp the LAA at, for example, a more proximal site, permitting further advancement of control element 40 toward the base of the LAA.

Once ligating element 30 is positioned around the base of the LAA, control element 40 can be removed if desired. For example, a clinician can pull on one end of control element 40 in the direction of the arrow shown in FIG. 7 to remove it entirely or partially from ligating element 30. In such an embodiment, the control element 40 is preferably slidably fitted within the ligating element 30, i.e., the control element 40 can be pulled out of the ligating element 30 while the ligating element 30 remains in its selected position (e.g., around an LAA, etc.). Alternatively, control element 40 can be left within ligating element 30.

Figure 8:
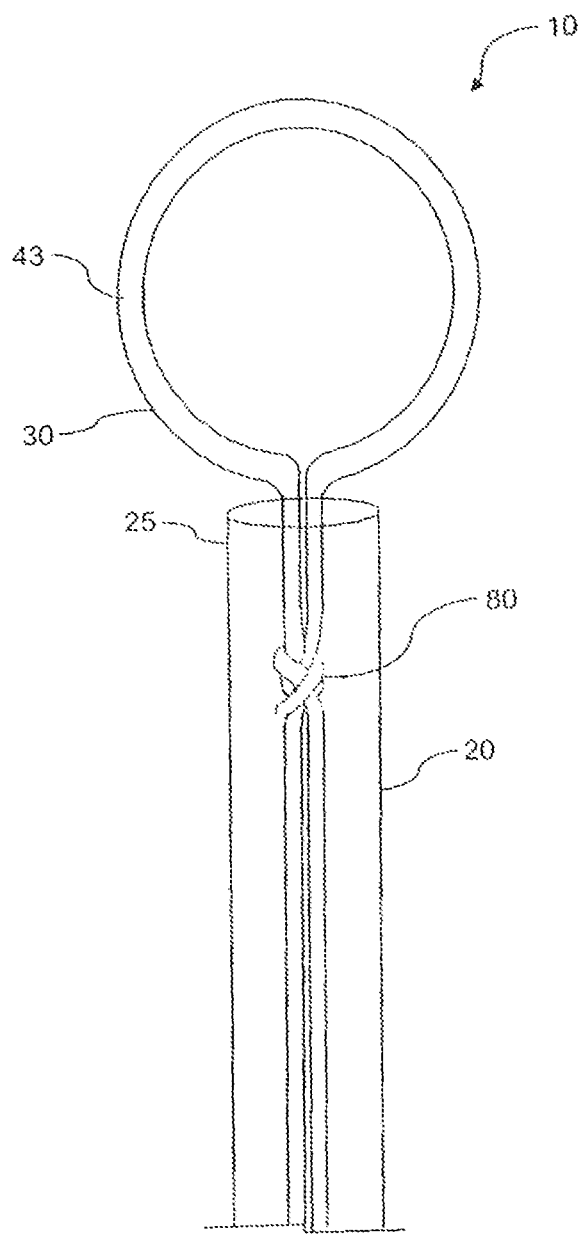
FIG. 8 is a cross-sectional view of the distal portion of the device as shown in FIG. 2, further depicting a knot in the ligating element.
Figure 9:
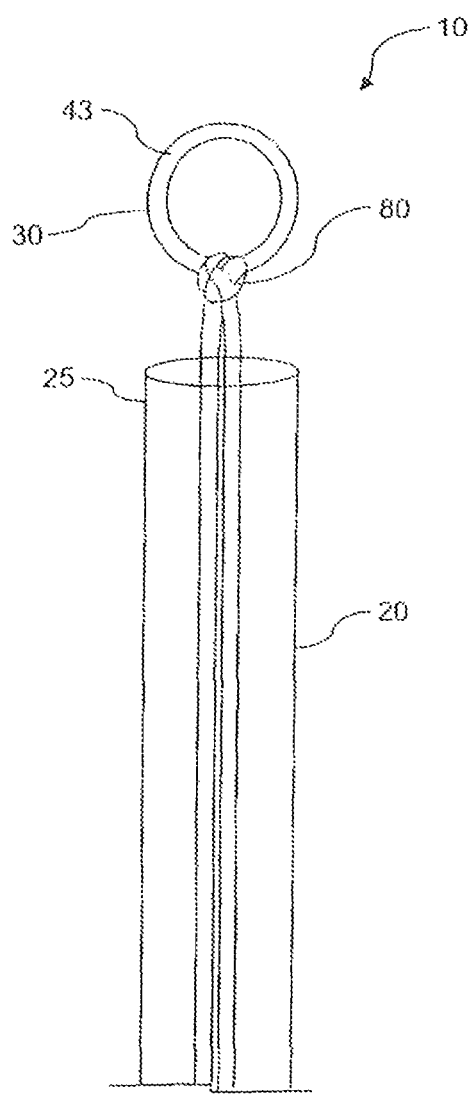
FIG. 9 is a cross-sectional view of the distal portion of the device as shown in FIG. 8, where the knot is advanced to the base of the lariat and the lariat is in a tightened configuration.

Ligating element 30 can be tightened and held in position around the LAA using any suitable retention means including, without limitation, a knot or a clip. For example, knot 80 can be tied in ligating element 30 at a position outside the body, and can be advanced along ligating element 30 through catheter 20 using any suitable method or device, including those known in the art (such as, e.g., a knot pusher (not shown)). FIG. 8 depicts knot 80 as it approaches distal end 25 of catheter 20, while FIG. 9 depicts knot 80 as it can appear in position at a tightened loop around the LAA. In some embodiments, a clip can be advanced through device 10 (e.g., through catheter 20 or through outer sheath 60) and positioned around ligating element 30.

Figure 10:
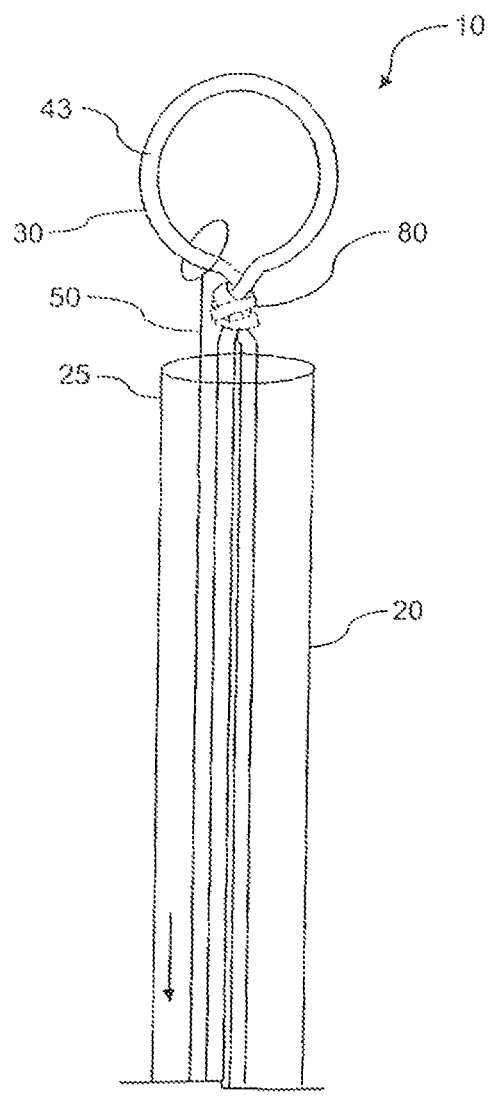
FIG. 10 is a cross-sectional view of the distal portion of the device as shown in FIG. 9, further including a repositioning element and depicting loosening of the knot.

In some embodiments, ligating device 10 can include a means for repositioning ligating element 30 after it has been tightened around the LAA. As shown in FIG. 10, for example, positioning element 50 can be used to reposition ligating element 30. By pulling positioning element 50 in the direction of the arrow shown in FIG. 10, a clinician can pull knot 90 toward catheter 20, such that ligating element 30 can be loosened and/or repositioned.

Figure 10A:
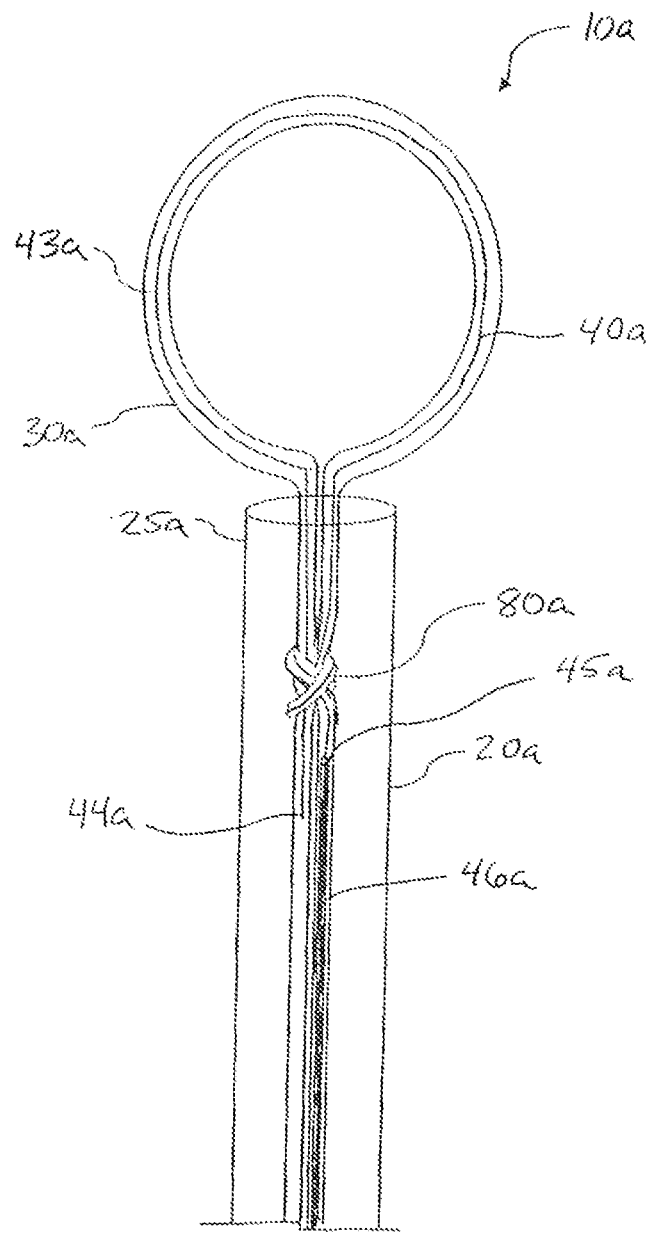
FIG. 10A is a cross-sectional view of a ligating device in which the control element is positioned through a knot formed in the ligating element.

In some embodiments, the control element threaded through the lumen of a hollow ligating element may include portions of different thickness. Referring to FIG. 10A, the catheter 20a has a distal end 25a from which the lariat or loop 43a formed in the ligating element 30a extends. A control element 40a extends through a lumen in the ligating element 30a. One feature of the ligating device depicted in FIG. 10A is that a knot 80a is formed in the ligating element 30a while the control element 40a is located in the portion of the ligating element 30a containing the knot 80a.

The control element 40a can include two or more different portions. For example, the control element 40a can include a distal portion located between the distal end 44a and the transition 45a, and a proximal portion located between the transition 45a and the proximal end (not shown) of the control element 40a. The proximal end of the control element 40a (not shown) may preferably extend outside of the proximal end (also not shown) of the catheter 20a.

An additional feature of the control element 40a depicted in FIG. 10A is that the thickness of the distal portion of the control element 40a (i.e., the portion between the distal end 44a and the transition 45a) is less than the thickness of the proximal portion of the control element 40a (i.e., the portion of the control element 40a from the transition 45a to the proximal end of the control element 40a). The thinner distal portion of the control element 40a may be thin enough such that the knot 80a can be formed in and advanced along the ligating element 30 such that the knot 80a is located proximate the distal end 25a of the catheter 20a before the lariat 43a is advanced out of the catheter 20a. In addition, the distal portion of the control element 40a may be thin enough such that, after deployment of the ligating element 30a, the control element 40a can be removed from the ligating element 30a by, e.g., pulling on the proximal end of the control element 40a such that the distal portion of the control element 40a is removed from the knot and the lariat or loop 43a.

Although the thickness differential in the control element 40a is depicted as occurring within a relatively small distance in the embodiment of FIG. 1 OA, the thickness of the control element 40a may change gradually over a significant distance, provided that the thickness of the control element 40a passing through the knot 80a does not prohibit removal of the control element 40a (if its removal is desired).

Figure 10B:
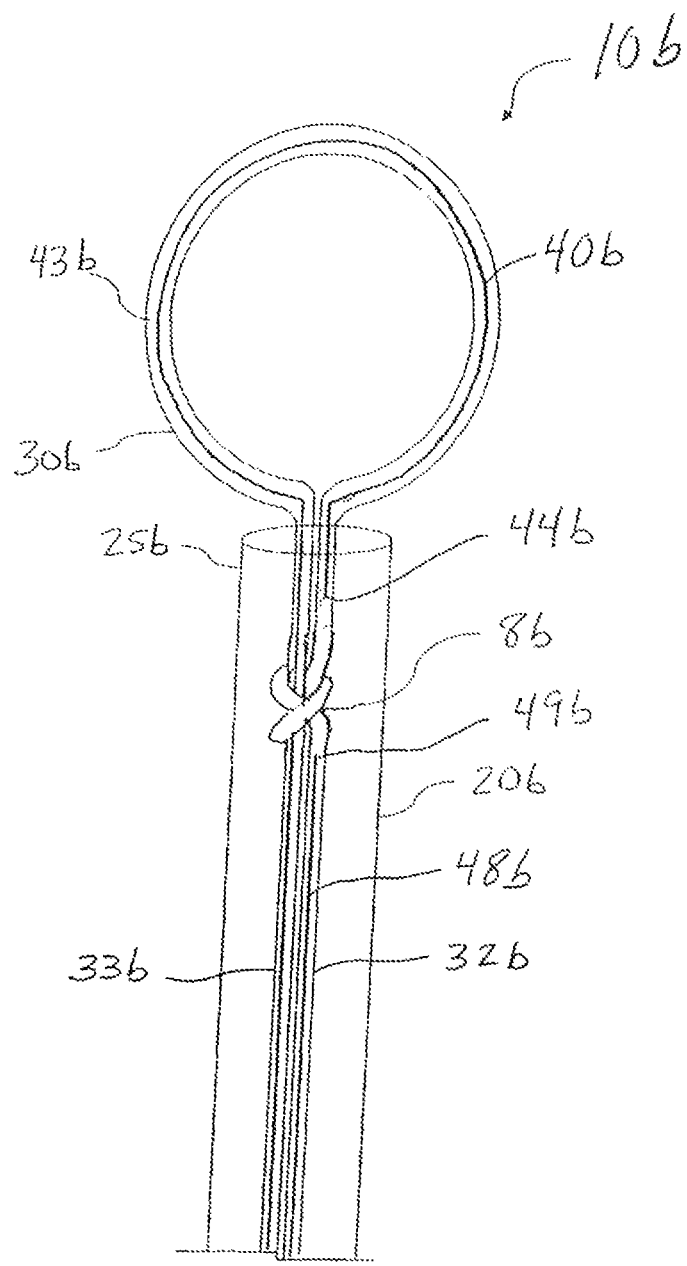
FIG. 10B is a cross-sectional view of a ligating device in which two control elements are positioned in the ligating element.

Another exemplary embodiment of a ligating device 10b is depicted in FIG. 10B. The depicted ligating device includes a primary control element 40b and a secondary control element 48b, both of which are threaded through portions of the ligating element 30b. As in previously described embodiments, the catheter 20b has a distal end 25b from which the lariat or loop 43b formed in the ligating element 30b extends.

The ligating element 30b includes a first portion 32b extending along the right side of the catheter 20b (as seen in FIG. 10B) towards the loop 43b. The ligating element 30b also includes a second portion 33b extending along the left side of the catheter 20b (as seen in FIG. 10B) towards the loop 43b. A knot 80b is formed in the ligating element 30b. More particularly, in the depicted embodiment, the knot 80b is formed in the portion 32b of the ligating element 30b, and the portion 33b of the ligating element 30b extends through the knot 80b. As a result, the knot 80b may be potentially referred to as a slip knot that can be advanced along the portion 33b while the control element 40b remains in position within the ligating element 30b.

The primary control element 40b preferably forms a loop 43b as depicted, with the ligating element 30b conforming to the shape of the loop 43b formed by the control element 40b. The primary control element 40b has a distal end 44b that may preferably be located distal of the knot 80b. In other words, the primary control element 40b may preferably not extend into the knot 80b as formed in portion 32b of the ligating element 30b. In another characterization, the primary control element 40b may be described as having a distal end 44b that is not located within or proximally of the knot 80b (as delivered for use in a subject).

Although the portion of the primary control element 40b within the left-hand portion 33b of the ligating element 30b does extend through the knot 80b, that portion 33b of the ligating element 80b is relatively straight and does not contain the bends associated with the knot 80b. As a result, the control element 40b may not need to be more rigid than, for example, the portion of the control element 40a that extends through the knot 80a in ligating device 10a as described in connection with FIG. 10A. That increased rigidity may assist in forming loop 43b in the ligating element 30b In some embodiments, it may be preferred that the distal end 44b of the primary control element 40b be located within the loop 43b (and not extend into the portion 32b of the ligating element 30b that leads to the loop 43b—see, for example, FIG. 7). Alternatively, the primary control element 40b can be withdrawn (retracted proximally) as the knot 80b is advanced distally such that the distal end 44b of the control element 40b remains outside of the knot 80b as formed in portion 32b of the ligating element 30b.

The ligating device 10b depicted in FIG. 10B includes an optional secondary control element 48b that extends through the portion 32b of the ligating element 30b. It may be preferred that the secondary control element 48b have a distal end 49b that is located proximally of the knot 80b such that the secondary control element 48b does not extend through the knot 80b. In some embodiments, the secondary control element 48b may be advanced distally as the knot 80b is advanced distally to provide support and rigidity to the portion 32b of the ligating element 30b as the knot is advanced.

Once the clinician has determined that ligating element 30 is in a suitable position and does not need to be moved, a suitable device (e.g., a scissors, scalpel, clipper, or any other useful device) can be advanced through device 10 (e.g., along positioning element 50) to cut ligating element 30 and control element 40, if applicable, proximate the retention means (e.g., knot 90). Ligating element 30 can be left in position around the base of the LAA, and the remainder of device 10 can be removed from the subject's body. Alternatively, if the position of ligating element 30 around the LAA is deemed unsuitable, the cutting device can be used to cut through lariat 43, permitting complete removal of ligating element 30.

Exemplary embodiments of the ligating devices in which the ligating element is formed of rigid material and the control element is formed of pliable material are depicted in FIGS. 11-15. Ligating device 110 can include catheter 120 with a proximal end (not shown) and distal end 125. Catheter 120 can contain ligating element 130 connected to elongate element 135, which can extend through the length of catheter 120. Catheter 120 also can contain control element 140, which can be disposed within all or a portion of ligating element 130.

Figure 11:
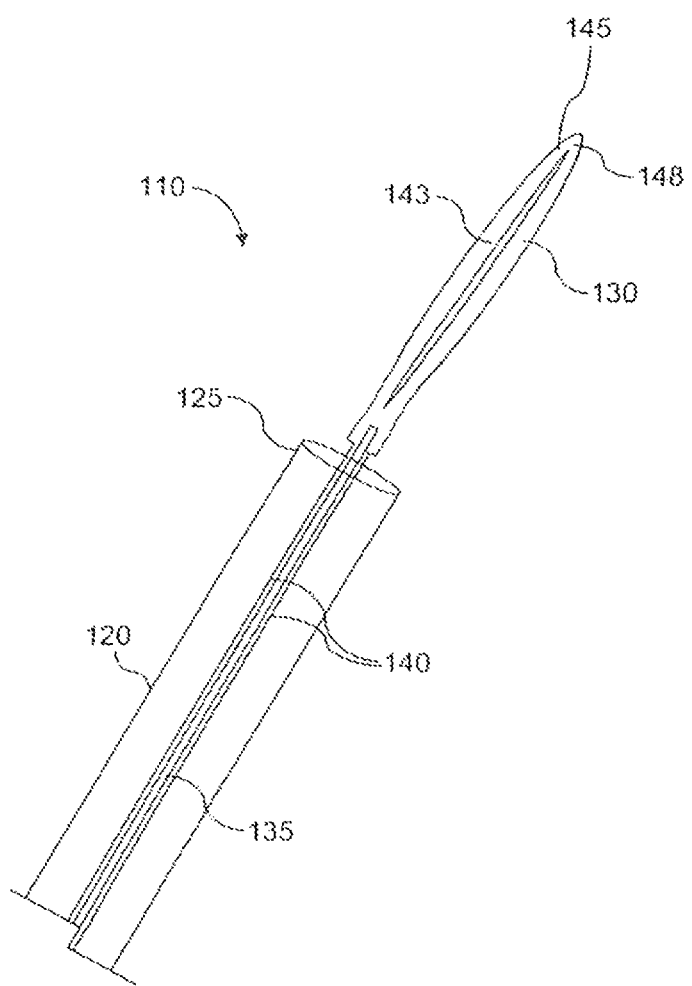
FIG. 11 is a side view of the distal portion of a device having a catheter and a rigid ligating element, where the ligating element is connected to an elongate element contained within the catheter, and further having a control element extending through the catheter and the ligating element. As shown, the ligating element is in a closed configuration.
Figure 12:
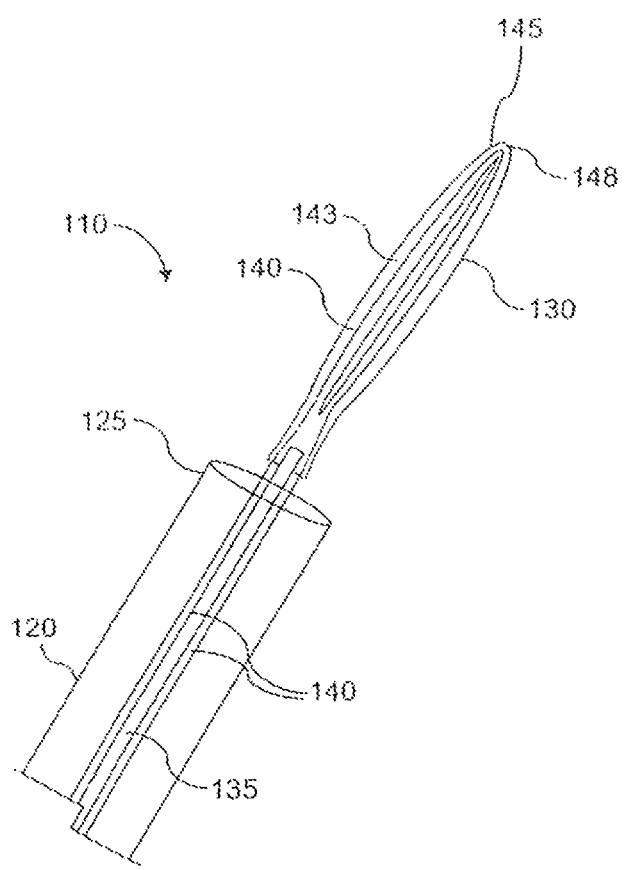
FIG. 12 is a cross-sectional view of the distal portion of the device depicted in FIG. 11, with the ligating element in a closed configuration.

In this embodiment, ligating element 130 can be formed of shape memory material (e.g., Nitinol), and control element 140 can be a suture or a pliable wire. Ligating element 130 can be configured to have an original shape that is closed, (e.g., a closed or flattened loop) as shown in FIGS. 11 and 12, for example. A clinician can advance ligating element 130 out of distal end 125, and then can open ligating element 130 by actuating control element 140.

Figure 13A:
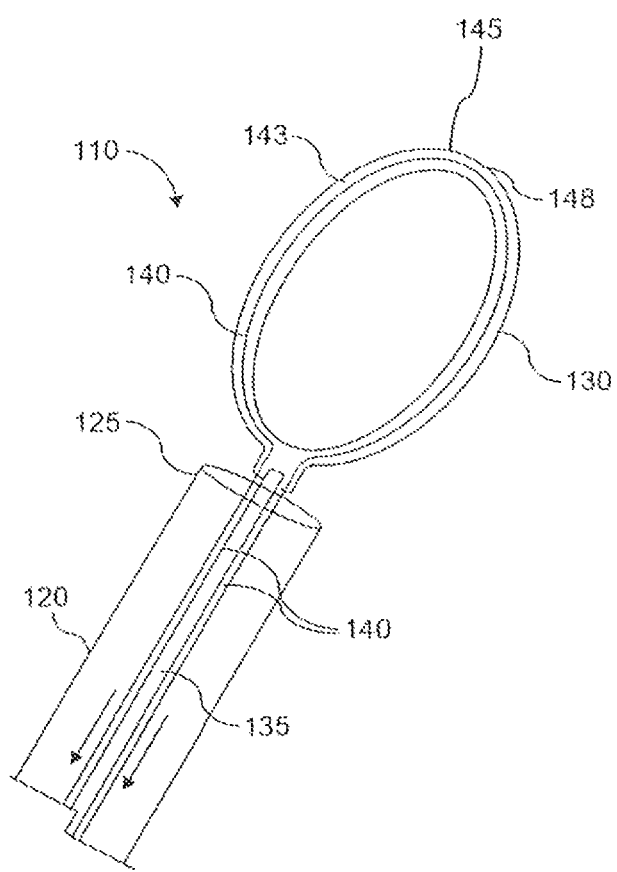
FIGS. 13A and 13B are cross-sectional views of the distal portion of devices having a control element extending through the entire ligating element (FIG. 13A) or through a portion of the ligating element (FIG. 13B), with the ligating element shown in an open configuration.

For example, with embodiments in which control element 140 extends through catheter 120, into and completely through ligating element 130, and back through catheter 120, (as depicted in FIGS. 12 and 13A), both ends of control element 140 can protrude from the proximal end of catheter 120. By pulling on both ends of control element 140 in the direction of the arrows shown in FIG. 13A, a clinician can actuate ligating element 130, causing it to open.

Figure 13B:
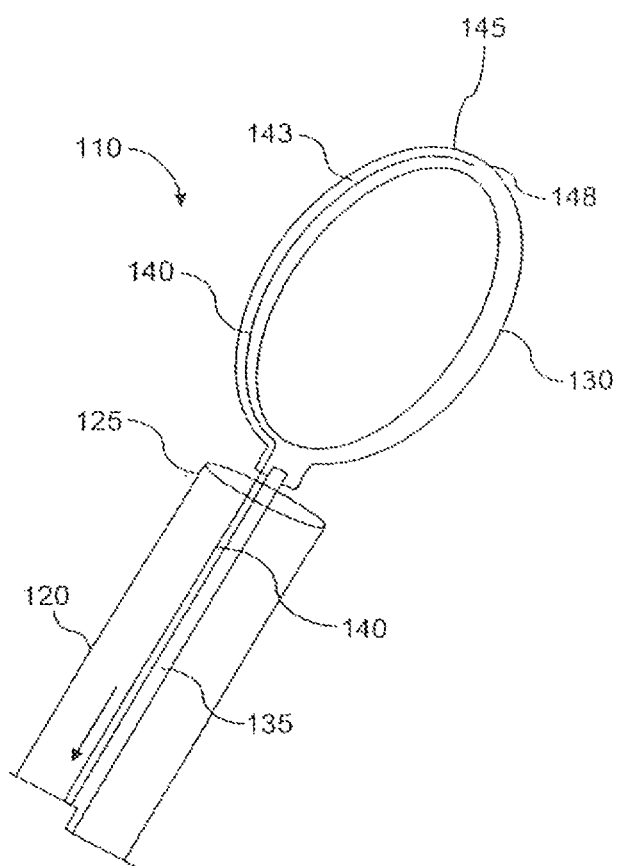

In other embodiments, control element 140 can extend through catheter 120 and into ligating element 130, where it can be secured at or near distal end 145 of ligating element 130 (e.g., at point 148). In such embodiments, as depicted in FIG. 13B, one end of control element can protrude from the proximal and of catheter 120. A clinician can pull on the protruding end of control element 140 to open ligating element 130. In either case, actuation of control element 140 can cause ligating element 130 to expand and form lariat 143, which can be suitable for positioning around the LAA.

Figure 14:
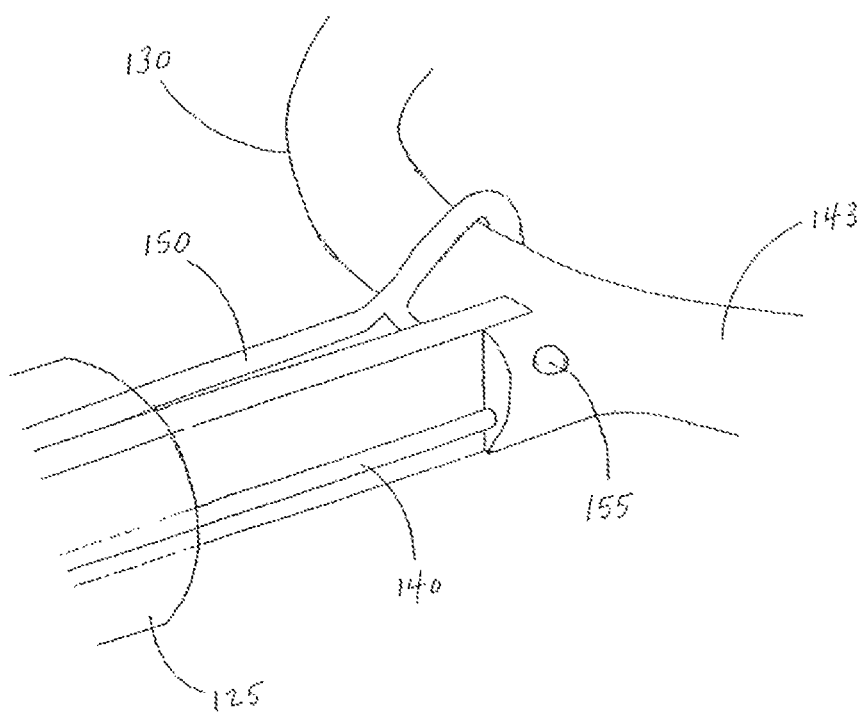
FIG. 14 is a side view of a portion of the distal end of the device depicted in FIG. 13, where the device further includes a positioning element.
Figure 15:
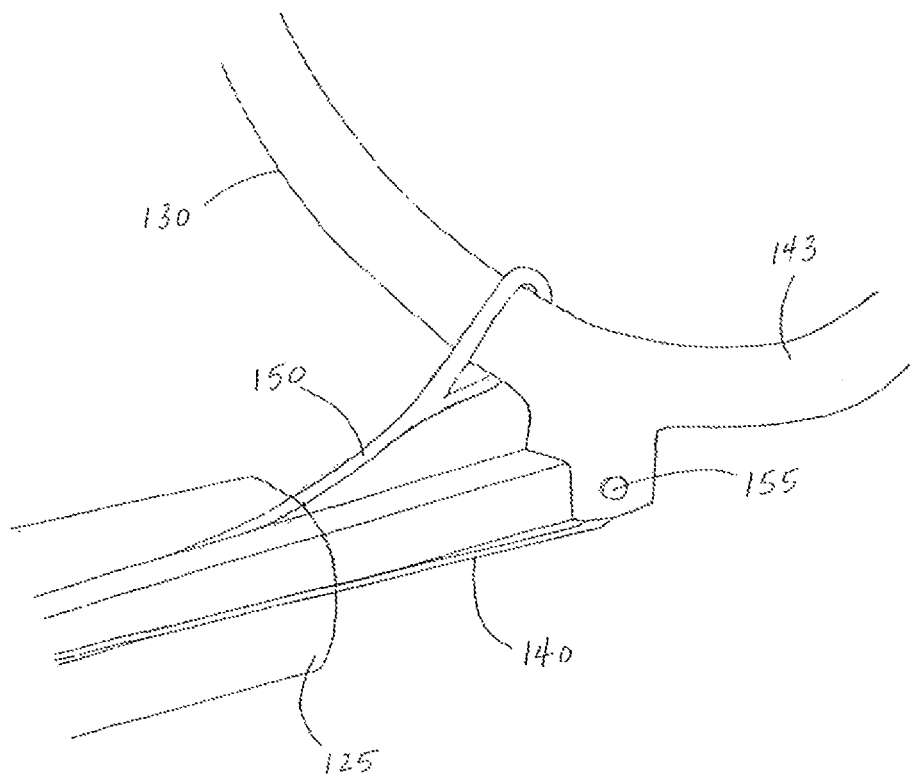
FIG. 15 is a side view of a portion of the distal end of the device depicted in FIG. 13, where the device further includes a positioning element, and where the ligating element is at an angle with respect to the elongate element.

Ligating device 110 can further include positioning element 150 and pivot pin 155, shown in FIGS. 14 and 15. Pivot pin 155 can be located at the junction of ligating element 130 and elongate element 135, and in some embodiments can be used to connect ligating element 130 to elongate element 135. Positioning element 150 can be contained within catheter 120, as shown in FIGS. 14 and 15, or can be contained within an outer sheath. Positioning element 150 can include loop 160 and elongate portion 165. Loop 160 can encircle a portion of ligating element 130. A clinician can pull on elongate portion 165 of positioning element 150 in the direction indicated by the arrow in FIG. 13. The resulting force of loop 160 on ligating element 130 can cause ligating element 130 to rotate about pivot pin 155, so that ligating element 130 is at an angle with respect to elongate element 135. Ligating element 130 can be adjusted to any suitable angle with respect to elongate element 135 (e.g., an angle of about 20, 30, 40, 45, 50, 60, 70, 80, 85, 90, 95, 100, 110, 120, 130, 135, 140, 145, or 150 degrees). Typically, positioning element 150 can be used to adjust the angle of ligating element 130 after lariat 143 is formed by pulling on control element 140. In some embodiments, however, the angle of ligating element 130 can be adjusted before or after lariat 143 is formed.

Once ligating element 130 is in place around the LAA, control element 140 can be released, allowing ligating element 130 to assume its original shape and thus tighten or close around the base of the LAA. Control element 140 can be removed from ligating element 130, or can be left within the interior of ligating element 130. After a clinician is satisfied with the position of ligating element 130 around the LAA, a suitable cutting or detaching device (e.g., a scissors, scalpel, clipper, or any other useful device) can be advanced through device 110 to detach ligating element 130 (and control element 140, if applicable) from elongate portion 135. Ligating element 130 can be left in position around the base of the LAA, and the remainder of device 110 can be retracted from the subject's body.

Figure 16:
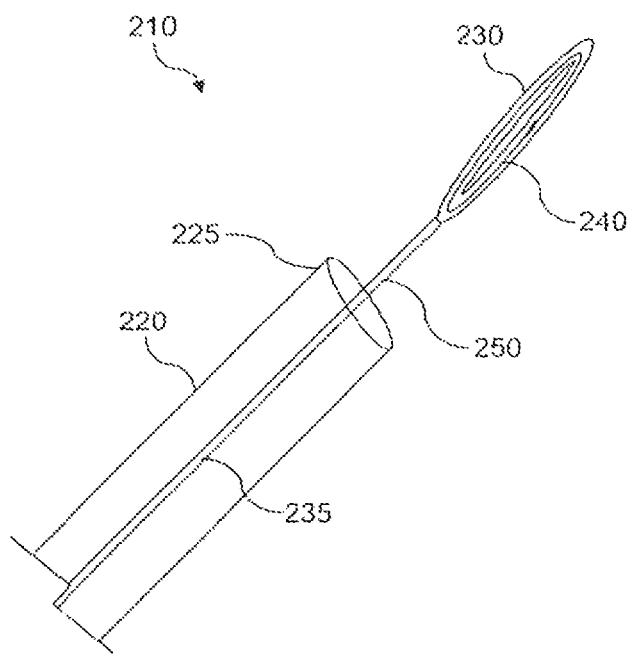
FIG. 16 is a cross-sectional view of the distal portion of a device having a catheter containing an elongate element, with a hollow control element connected to the elongate element, and a rigid ligating element contained within the hollow control element. The control and ligating elements are shown in a closed (e.g., uninflated) configuration.
Figure 17:
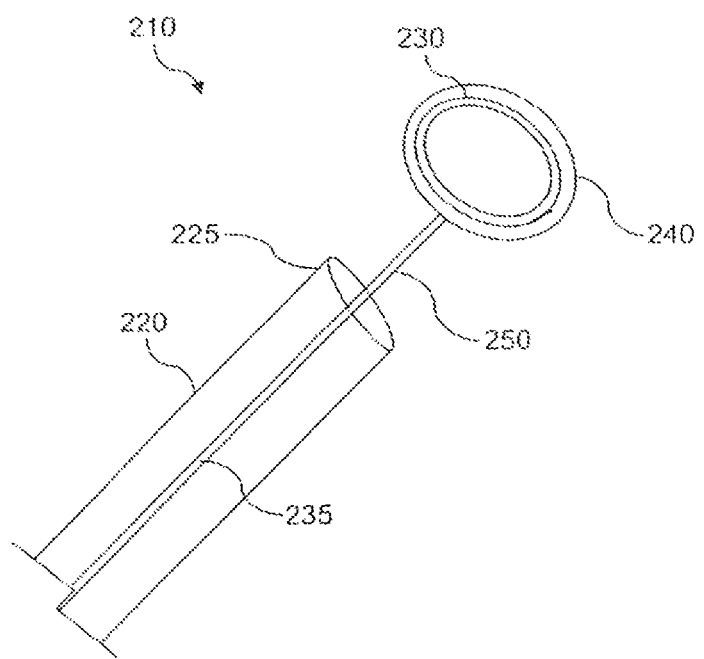
FIG. 17 is a cross-sectional view of the distal portion of the device shown in FIG. 16, where the control and ligating elements are in an open (e.g., inflated) configuration.
Figure 18:
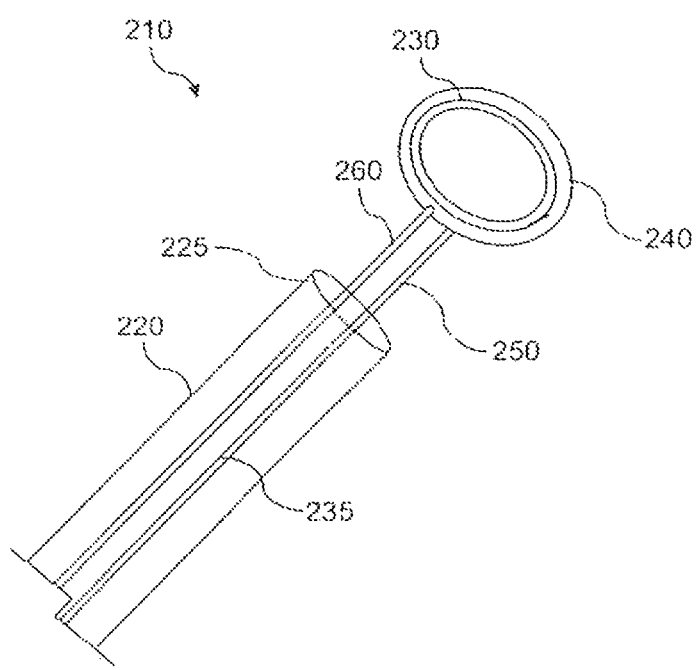
FIG. 18 is a cross-sectional view of the distal portion of the device shown in FIG. 17, where the device further includes a positioning element.

In the exemplary embodiments depicted in FIGS. 16-18, ligating device 210 can have catheter 220 with a proximal end (not shown) and distal end 225, with ligating element 230, elongate element 235, and hollow donut-shaped control element 240 contained therein. Elongate element 235 can extend through the length of catheter 220, and control element 240 can be connected to elongate element 235 and positioned at or near distal end 225. Ligating element 230 can be contained within control element 240, as shown in FIGS. 16-18, or can encircle the outer circumference of control element 240.

In some embodiments, ligating element 230 can be a ring clip whose natural position is closed (i.e., in the absence of external forces, the ligating element 230 is in the closed position as depicted in FIG. 16). Ligating element 230 can be formed of, e.g., Nitinol or any other suitable shape memory material. Control element 240 can be formed of soft pliable material (e.g., PTFE, polyethylene, or polypropylene) that is air tight. Control element 240 also can provide an atraumatic covering for ligating element 230 if ligating element 230 is contained within control element 240, or can serve as a tissue protector if ligating element 230 extends around the circumference of control element 240.

In some embodiments, ligating device 210 includes a conduit in fluid communication with control element 240. For example, elongate element 235 can be conduit 250 in fluid communication with the interior of control element 240. Alternatively, ligating device 210 can include a separate fluid conduit. Conduit 250 can have a length such that it can extend through catheter 220 (or through an outer sheath containing catheter 220, if applicable) between the proximal end and distal end 225. A clinician can pass fluid into conduit 250 from outside the subject's body. In these embodiments, ligating device 210 can be deployed by inflating control element 240 with, for example, a gas (e.g., air, oxygen, or nitrogen) or a liquid (e.g., saline or water) passed through conduit 250. Inflation of control element 240 can cause ligating element 230 to open, forming lariat 243.

In some embodiments, ligating device 210 can further include positioning element 260, shown in FIG. 18. Positioning element 260 can have a length such that it can extend through catheter 220 between the proximal end and distal end 225. In some embodiments, positioning element 260 can be reversibly attached to control element 240.

A clinician can then position ligating device 210 at the base of the LAA and deflate control element 240 to close ligating element 230. For example, a clinician can remove conduit 250 from control element 240. The removal of conduit 250, in combination with inward pressure exerted by ligating element 230, can cause control element 240 to deflate. Once device 210 is positioned around the base of the LAA and deflated, a clinician can detach fluid conduit 250 and positioning element 260, if applicable, from ligating element 230 and control element 240. The remainder of ligating device 210 can be removed from the subject's body, while ligating element 230 and control element 240 remain.

Figure 19:
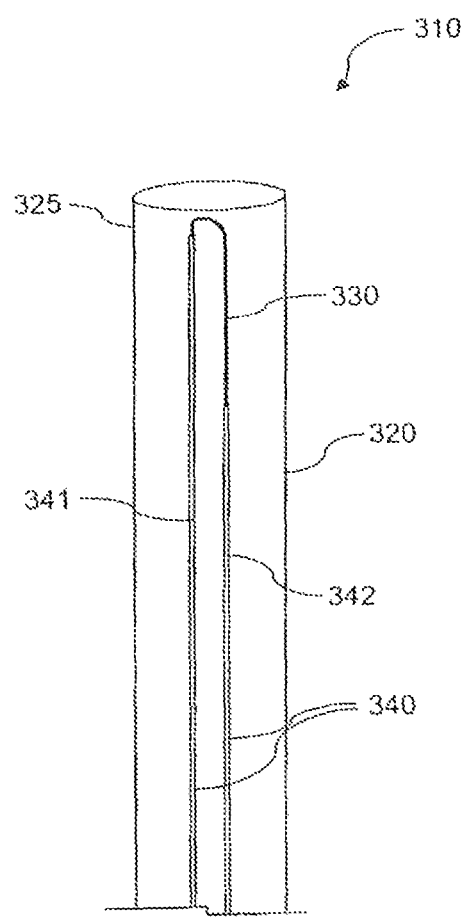
FIG. 19 is a cross-sectional view of the distal portion of a device having a control element that includes two substantially rigid elongate portions, and a flexible ligating element attached to the distal ends of the elongate portions.
Figure 20:
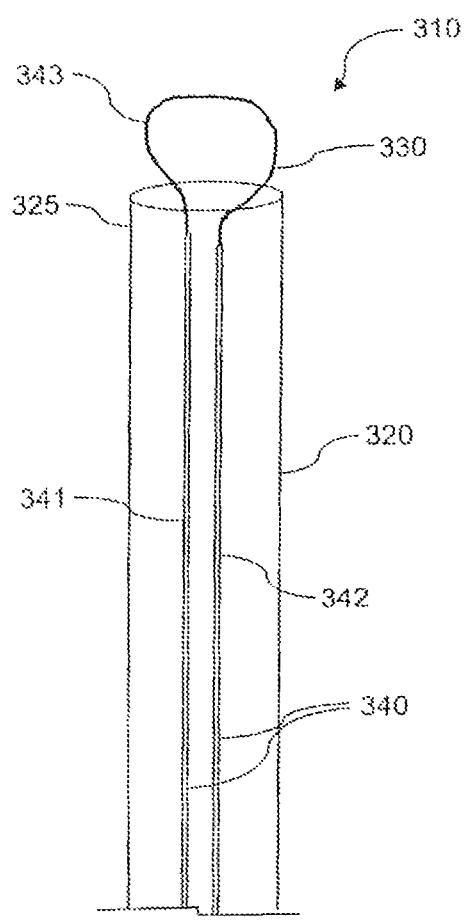
FIG. 20 is a cross-sectional view of the distal portion of the device of FIG. 19, where the elongate portions of the control element have been manipulated such that the flexible ligating element forms a lariat.

In the exemplary embodiments depicted in FIGS. 19 and 20, ligating device 310 can include catheter 320 with a proximal end (not shown) and distal end 325. Ligating element 330 and control element 340 can be positioned within catheter 320. Control element 340 can include first elongate portion 341 and second elongate portion 342. Ligating element 330 can be attached to the distal ends of elongate portions 341 and 342. A clinician can manipulate first and second elongate portions 341 and 342 with respect to one another, and can cause ligating element 330 to form lariat 343, as shown in FIG. 20. Lariat 343 can be positioned around the base of the LAA, and a clip or other suitable fastening means can be passed through catheter 320 to retain ligating element 330 in position. A cutting device can be used to sever lariat 343 from the remainder of ligating element 330, and the device can be removed from the subject's body.

Figure 21:
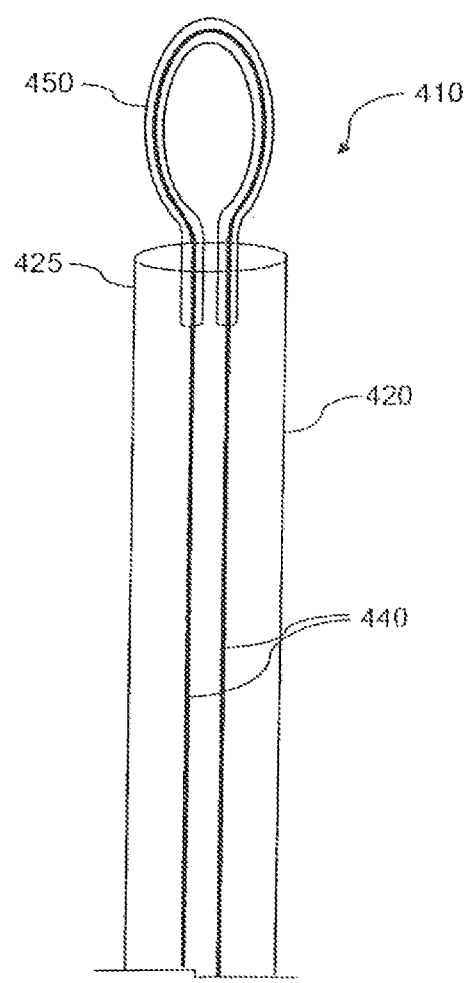
FIG. 21 is a cross-sectional view of the distal portion of a device having a catheter, a control element, and a protective sheath.
Figure 22:
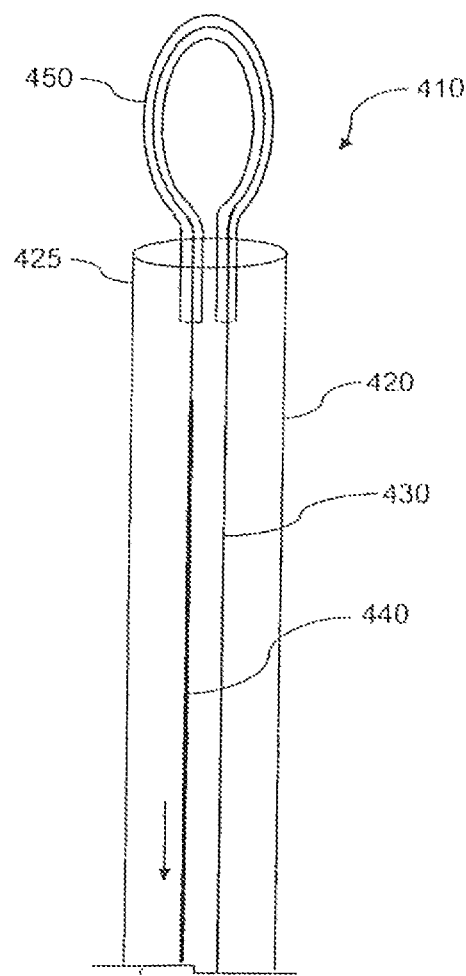
FIG. 22 is a cross-sectional view of the distal portion of the device of FIG. 21, with the control element pulled through the catheter such that a ligating element connected to the control element is advanced through the protective sheath.

In the exemplary embodiments shown in FIGS. 21 and 22, ligating device 410 includes a catheter 420 with a proximal end (not shown) and distal end 425, wherein control element 440 is positioned within the lumen of catheter 420. Control element 440 can be formed using a substantially rigid material (e.g., wire). Control element 440 can have a generally elongate "U" shape, such that it can extend through the length of catheter 420, with both ends protruding from the proximal end of catheter 420 and the bottom of the "U" positioned at or near distal end 425 of catheter 420. A lariat or loop can form when the distal end of control element 440 is advanced out of distal end 425, as shown in FIG. 21.

Ligating element 430 can be attached to one end of control element 440, and can be, for example, a suture. Device 410 also can include a guard 450, which can be a hollow, flexible suture or sheath that covers the portion of control element 440 that is to be placed around the LAA (or other anatomical structure). Although the guard 450 is depicted as terminating relatively close to the loop, the guard 450 could alternatively extend towards the proximal end of the catheter 420 (even as far as extending out of the proximal end of the catheter 420).

Device 410 also can include a positioning element (not shown) to facilitate placement of control element 440 (around, e.g., the base of the LAA). When control element 440 is suitably positioned around the LAA, a clinician can pull on the free end of control element 440 in the direction indicated by the arrow in FIG. 22, advancing ligating element 430 toward distal end 425 of catheter 420 and through guard 450, as shown in FIG. 22, such that ligating element 430 takes the place of the control element 440 and is positioned around the LAA. Any suitable mechanism (e.g., a clip or a knot and described herein) then can be used to retain ligating element 430 in position. Excess portions of ligating element 430 (e.g., portions that are not positioned around the LAA) can be cut, and the device can be removed from the subject's body.

Figure 23:
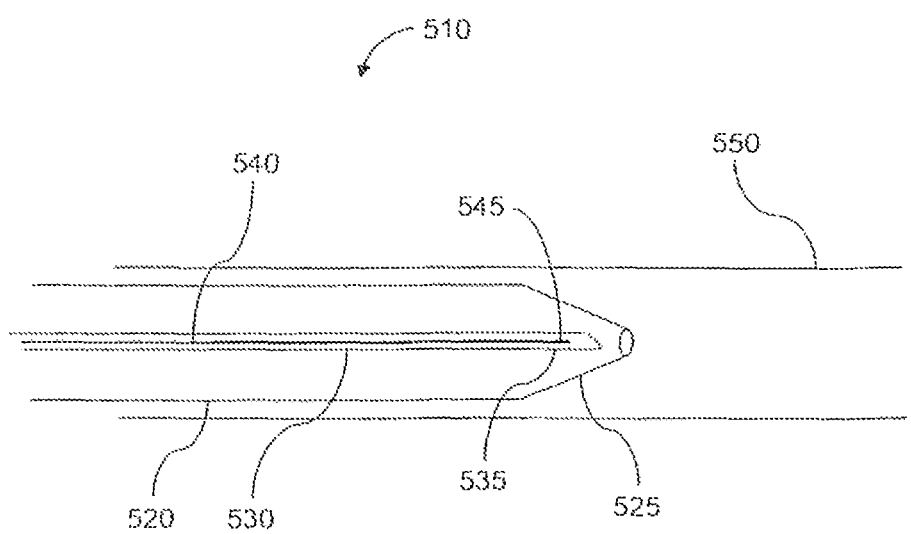
FIG. 23 is a cross-sectional view of the distal portion of a device for accessing the pericardial space through the coronary sinus (CS).
Figure 24:
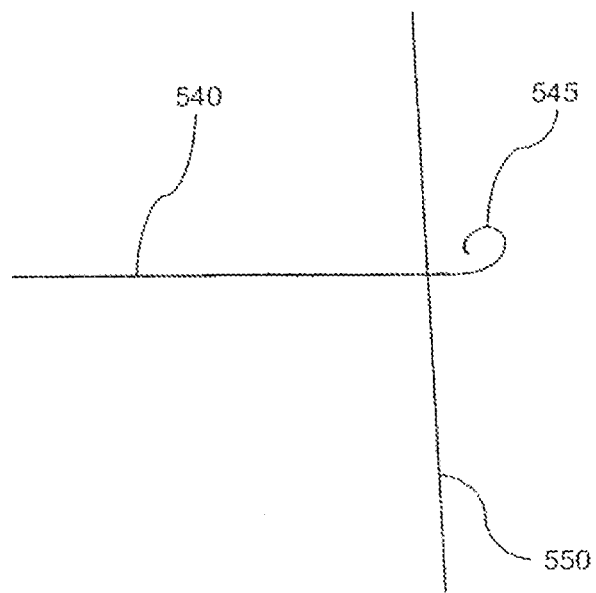
FIG. 24 is a side view of the distal end of a wire that coils when deployed through the CS wall.

The devices depicted in FIGS. 23 through 26 are examples of devices that can be used for placement of a ligating device via the CS. Device 510 can include sheath 520, hollow needle 530, and wire 540, which can each have a proximal end (not shown) and distal ends 525, 535, 545, respectively. In some embodiments, device 510 does not include needle 530. As shown in FIGS. 23 and 24, distal end 525 of sheath 520 can be tapered. In some embodiments, distal end 525 is not tapered.

Figure 25:
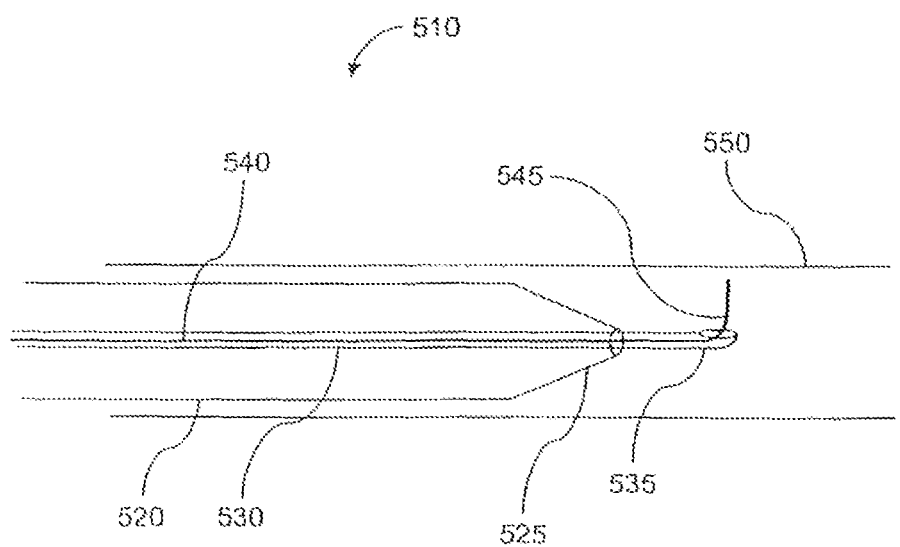
FIG. 25 is a cross-sectional view of the distal portion of the device of FIG. 23, having a needle with a curved distal end.

Device 510 can be advanced into CS 550, and needle 530 and/or wire 540 can pierce the wall of CS 550. Any suitable methods can be used to pierce the wall of CS 550 and to prevent wire 540 or needle 530 from puncturing the pericardial sac. As depicted in FIG. 24, for example, distal end 545 of wire 540 can be configured to coil after being deployed out of device 510 and through the wall of CS 550. As shown in FIG. 25, distal end 535 of needle 530 can be curved, such that when distal end 545 of wire 540 exits needle 530, it is directed toward the wall of CS 550.

Figure 26:
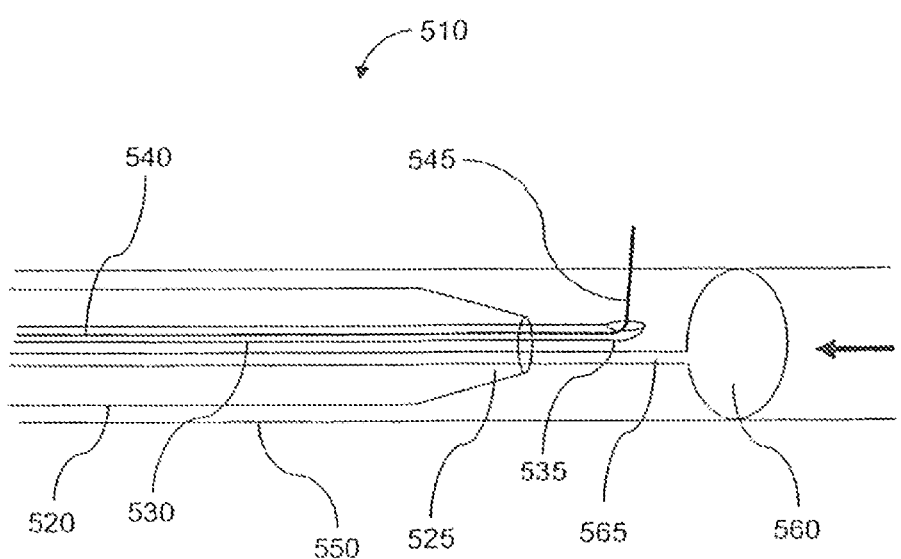
FIG. 26 is a cross-sectional view of the distal portion of the device shown in FIG. 25, further including a balloon connected to a fluid conduit.

In some embodiments, means can be used to reduce or prevent the flow of blood from out of the CS and into the pericardial space. As shown in FIG. 26, for example, balloon 560 can be passed through device 510, and can be inflated within the lumen of the CS. Balloon 560 can be connected to fluid conduit 565, through which a fluid such as air, oxygen, saline, or water, for example, can be passed to inflate and deflate balloon 560. Balloon 560 can be passed through sheath 520 in an uninflated state, and can be inflated once it is within the lumen of the CS. When inflated, balloon 560 can reduce the flow of blood, indicated by the arrow in FIG. 26, into the pericardial space through the opening created by wire 540.

Figure 27:
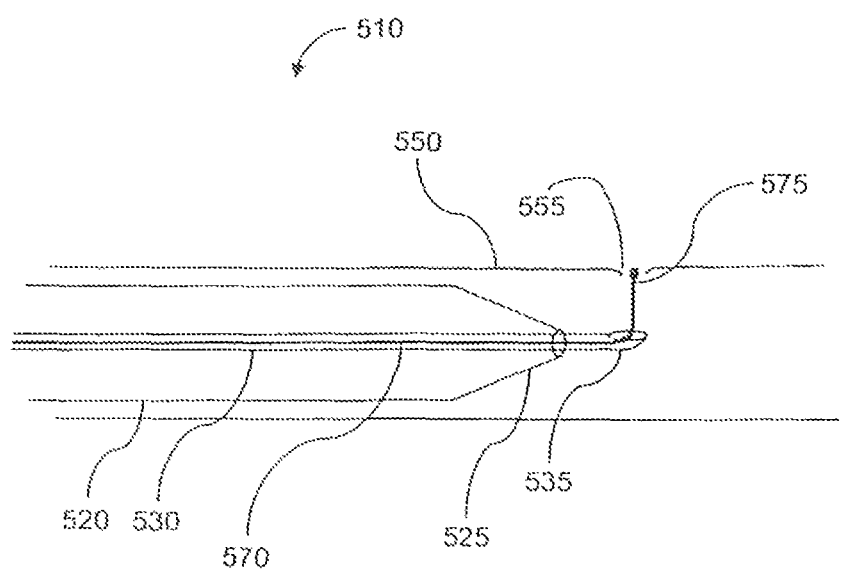
FIG. 27 is a cross-sectional view of the distal portion of the device of FIG. 25, having a wire with a radiofrequency (RF) electrode at its tip.

In some embodiments, device 510 also can include means for closing an opening in the CS wall after completion of a procedure (e.g., ligation of the LAA, atrial ablation, or pericardial mapping) within the pericardial space. In some cases, a wire having a RF tip at its distal end can be passed through the sheath or the needle of a device. Once the tip of the wire reaches the opening in the CS wall, RF energy can be used to weld the opening. For example, as depicted in FIG. 27, device 510 can contain wire 570 having RF tip 575. As shown, wire 570 can be advanced through needle 530 until RF tip 575 reaches opening 555 in the wall of CS 550, and RF energy can be applied to weld tissue adjacent to opening 555.

Figure 28:
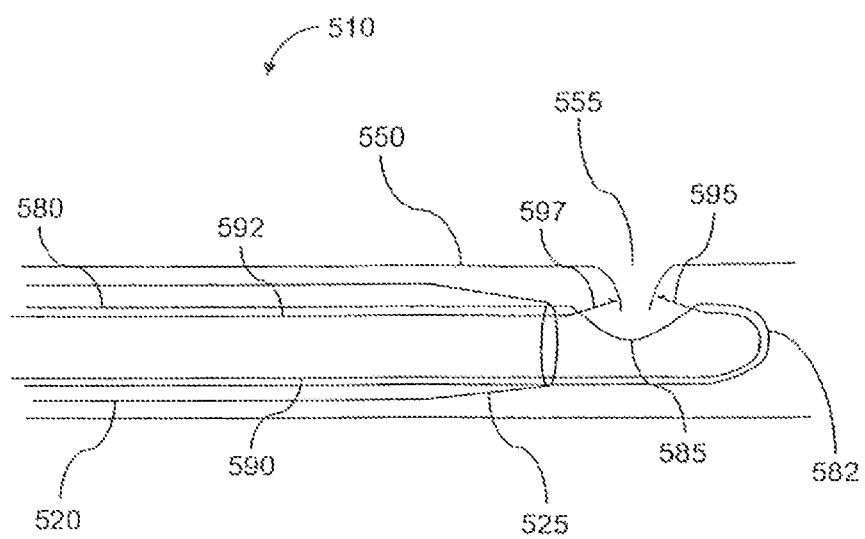
FIG. 28 is a cross-sectional view of the distal portion of a device for accessing the pericardial space through the CS, where the device contains a catheter having suture needles disposed therein.

In some cases, a suction device having needles or RF tipped wires disposed therein can be used to close an opening in the CS wall. As shown in FIG. 28, for example, device 510 can have hollow suction catheter 580 extending therethrough. Suction catheter 580 can have a proximal end (not shown), distal end 582 and side opening 585, and can contain (e.g., within its lumen or within longitudinal channels within its walls) needles 590 and 592, which can have distal ends 595 and 597, respectively. Suction catheter 580 can be advanced through sheath 520 until side opening 585 is positioned adjacent to opening 555 in the wall of CS 550. Suction can be used to pull tissue around opening 555 into side opening 585 of catheter 580, and needles 590 and 592 can be manipulated to physically suture tissue adjacent to opening 555. Once opening 555 is suitably closed, device 510 can be withdrawn from the subject's body.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of ligating a left atrial appendage, the method comprising:
  advancing a distal end of a catheter of a ligating device into a pericardial space while a proximal end of the catheter remains outside of the pericardial space, wherein the ligating device comprises:
    a ligating element located within the catheter, wherein the ligating element comprises a lumen and a first end and a second end, wherein the first end and the second end protrude from the proximal end of the catheter; and
    a control element located within the lumen of the ligating element, the control element comprising a first end that protrudes from the first end of the ligating element;
  advancing a distal portion of the ligating element and the control element contained therein out of the distal end of the catheter after advancing the distal end of the catheter into the pericardial space, wherein the control element forces the distal portion of the ligating element to form an open loop upon exit from the distal end of the catheter;
  positioning the open loop around a left atrial appendage in the pericardial space;

tightening the open loop around the left atrial appendage after positioning the open loop around the left atrial appendage in the pericardial space;

loosening the open loop after tightening the open loop;

repositioning the open loop around the left atrial appendage after loosening the open loop;

tightening the open loop around the left atrial appendage after repositioning the open loop around the left atrial appendage;

fixing the loop in position around the left atrial appendage after tightening the open loop around the left atrial appendage;

removing the control element from the lumen in the distal portion of the ligating element after positioning the open loop around the left atrial appendage in the pericardial space;

severing the ligating element after fixing the loop in position around the left atrial appendage such that the loop remains in position around the left atrial appendage after the severing; and removing the catheter from the pericardial space after severing the ligating element while the loop remains in position around the left atrial appendage after the catheter has been removed from the pericardial space.

2. A method according to claim 1, wherein removing the control element comprises pulling on the first end of the control element after the loop is positioned around the left atrial appendage.

3. A method according to claim 1, wherein removing the control element from the lumen of the ligating element comprises completely removing the control element from the lumen of the ligating element.

4. A method according to claim 1, wherein removing the control element from the lumen of the ligating element comprises only partially removing the control element from the lumen of the ligating element.

5. A method according to claim 1, wherein the method further comprises changing an angle of the open loop with respect to an elongate portion of the ligating element by adjusting the amount of the ligating element advanced out of the distal end of the catheter.

6. A method according to claim 1, wherein the method further comprises changing a size of the open loop formed by the distal portion of the ligating element by adjusting the amount of the ligating element advanced out of the distal end of the catheter.

7. A method according to claim 1, wherein advancing the distal end of the catheter into the pericardial space comprises advancing the distal end of the catheter in the pericardial space through an exterior of the pericardium defining the pericardial space.

8. A method according to claim 1, wherein advancing the distal end of the catheter into the pericardial space comprises advancing the distal end of the catheter between ribs to the pericardium.

9. A method according to claim 1, wherein advancing the distal end of the catheter into the pericardial space comprises advancing the distal end of the catheter between the xiphoid process and adjacent intercostal cartilage before the distal end of the catheter reaches the pericardial space.

10. A method according to claim 1, wherein advancing the distal end of the catheter into the pericardial space comprises advancing the distal end of the catheter into the chest cavity above the sternum and advancing the distal end of the catheter inferiorly toward the pericardial space.

11. A method of ligating a left atrial appendage, the method comprising:

advancing a distal end of a catheter of a ligating device into a pericardial space while a proximal end of the catheter remains outside of the pericardial space, wherein the ligating device comprises:

a ligating element located within the catheter, wherein the ligating element comprises a lumen and a first end and a second end, wherein the first end and the second end protrude from the proximal end of the catheter; and a control element located within the lumen of the ligating element, the control element comprising a first end that protrudes from the first end of the ligating element;

advancing a distal portion of the ligating element and the control element contained therein out of the distal end of the catheter after advancing the distal end of the catheter into the pericardial space, wherein the control element forces the distal portion of the ligating element to form an open loop upon exit from the distal end of the catheter;

changing a size of the open loop formed by the distal portion of the ligating element by adjusting the amount of the ligating element advanced out of the distal end of the catheter;

positioning the open loop around a left atrial appendage in the pericardial space;

tightening the open loop around the left atrial appendage after positioning the open loop around the left atrial appendage in the pericardial space;

loosening the open loop after tightening the open loop;

repositioning the open loop around the left atrial appendage after loosening the open loop;

tightening the open loop around the left atrial appendage after repositioning the open loop around the left atrial appendage;

fixing the loop in position around the left atrial appendage after tightening the open loop around the left atrial appendage;

removing the control element from the lumen in the distal portion of the ligating element after positioning the open loop around the left atrial appendage in the pericardial space, wherein removing the control element comprises pulling on the first end of the control element after the loop is positioned around the left atrial appendage;

severing the ligating element after fixing the loop in position around the left atrial appendage such that the loop remains in position around the left atrial appendage after the severing; and removing the catheter from the pericardial space after severing the ligating element while the loop remains in position around the left atrial appendage after the catheter has been removed from the pericardial space.

12. A method according to claim 11, wherein removing the control element from the lumen of the ligating element comprises completely removing the control element from the lumen of the ligating element.

13. A method according to claim 11, wherein removing the control element from the lumen of the ligating element comprises only partially removing the control element from the lumen of the ligating element.

14. A method according to claim 11, wherein the method further comprises changing an angle of the open loop with respect to an elongate portion of the ligating element by adjusting the amount of the ligating element advanced out of the distal end of the catheter.

15. A method according to claim 11, wherein advancing the distal end of the catheter into the pericardial space comprises advancing the distal end of the catheter in the pericardial space through an exterior of the pericardium defining the pericardial space.

16. A method according to claim 11, wherein advancing the distal end of the catheter into the pericardial space comprises advancing the distal end of the catheter between ribs to the pericardium.

17. A method according to claim 11, wherein advancing the distal end of the catheter into the pericardial space comprises advancing the distal end of the catheter between the xiphoid process and adjacent intercostal cartilage before the distal end of the catheter reaches the pericardial space.

18. A method according to claim 11, wherein advancing the distal end of the catheter into the pericardial space comprises advancing the distal end of the catheter into the chest cavity above the sternum and advancing the distal end of the catheter inferiorly toward the pericardial space.

19. A method of ligating a left atrial appendage, the method comprising:
- advancing a distal end of a catheter of a ligating device into a pericardial space through an exterior of a pericardium defining the pericardial space while a proximal end of the catheter remains outside of the pericardial space, wherein advancing the distal end of the catheter into the pericardial space comprises advancing the distal end of the catheter between the xiphoid process and adjacent intercostal cartilage before the distal end of the catheter reaches the pericardial space, wherein the ligating device comprises:
  - a ligating element located within the catheter, wherein the ligating element comprises a lumen and a first end and a second end, wherein the first end and the second end protrude from the proximal end of the catheter; and
  - a control element located within the lumen of the ligating element, the control element comprising a first end that protrudes from the first end of the ligating element;
- advancing a distal portion of the ligating element and the control element contained therein out of the distal end of the catheter into the pericardial space after advancing the distal end of the catheter into the pericardial space, wherein the control element forces the distal portion of the ligating element to form an open loop upon exit from the distal end of the catheter;
- positioning the open loop around a left atrial appendage in the pericardial space;
- tightening the open loop around the left atrial appendage after positioning the open loop around the left atrial appendage in the pericardial space;
- loosening the open loop after tightening the open loop;
- repositioning the open loop around the left atrial appendage after loosening the open loop;
- tightening the open loop around the left atrial appendage after repositioning the open loop around the left atrial appendage;
- fixing the loop in position around the left atrial appendage after tightening the open loop around the left atrial appendage;
- removing the control element from the lumen in the distal portion of the ligating element after positioning the open loop around the left atrial appendage in the pericardial space, wherein removing the control element comprises pulling on the first end of the control element after the loop is positioned around the left atrial appendage;
- severing the ligating element after fixing the loop in position around the left atrial appendage such that the loop remains in position around the left atrial appendage after the severing; and
- removing the catheter from the pericardial space after severing the ligating element while the loop remains in position around the left atrial appendage after the catheter has been removed from the pericardial space.

20. A method according to claim 19, wherein removing the control element from the lumen of the ligating element comprises completely removing the control element from the lumen of the ligating element.

* * * * *